United States Patent
Ho et al.

(10) Patent No.: US 8,051,855 B2
(45) Date of Patent: Nov. 8, 2011

(54) RESPIRATORY MASK

(75) Inventors: Peter Chi Fai Ho, Pittsburgh, PA (US); Eugene N. Scarberry, Trafford, PA (US); Jian-An Jiang, Shezhen (CN); Lance Busch, Trafford, PA (US)

(73) Assignee: RIC Investments, LLC, Wilmington, DE (US)

( * ) Notice: Subject to any disclaimer, the term of this patent is extended or adjusted under 35 U.S.C. 154(b) by 1135 days.

(21) Appl. No.: 11/599,133

(22) Filed: Nov. 13, 2006

(65) Prior Publication Data

US 2007/0107733 A1    May 17, 2007

Related U.S. Application Data

(60) Provisional application No. 60/736,709, filed on Nov. 15, 2005.

(51) Int. Cl.
A62B 18/02    (2006.01)

(52) U.S. Cl. ......... 128/206.21; 128/206.24; 128/206.26; 128/206.28

(58) Field of Classification Search ............. 128/200.24, 128/205.35, 206.12–206.16, 206.21, 206.24, 128/206.26, 206.28, 207.11
See application file for complete search history.

(56) References Cited

U.S. PATENT DOCUMENTS

| | | |
|---|---|---|
| 790,057 A | 5/1905 | Hively |
| 1,206,045 A | 11/1916 | Smith |
| 2,313,999 A | 3/1943 | Kreiselman |
| 2,535,938 A | 12/1950 | Lombard |
| 2,625,155 A | 1/1953 | Engelder |
| 2,749,910 A | 6/1956 | Faulconer, Jr. |
| 2,765,788 A | 10/1956 | Raiche |
| 2,875,757 A | 3/1959 | Galleher, Jr. |
| 3,042,035 A | 7/1962 | Coanda |
| 4,062,357 A | 12/1977 | Laerdal |
| 4,201,205 A | 5/1980 | Bartholomew |
| 4,347,205 A | 8/1982 | Stewart |
| 4,665,570 A | 5/1987 | Davis |
| D293,613 S | 1/1988 | Wingler |
| 4,803,981 A | 2/1989 | Vickery |
| 4,807,617 A | 2/1989 | Nesti |
| 4,907,584 A | 3/1990 | McGinnis |
| 4,913,401 A | 4/1990 | Handke |
| 4,971,051 A | 11/1990 | Toffolon |
| D323,908 S | 2/1992 | Hollister et al. |
| 5,121,745 A | 6/1992 | Israel |
| 5,562,324 A | 10/1996 | Massara et al. |
| 5,647,357 A | 7/1997 | Barnett et al. |
| 5,738,094 A | 4/1998 | Hoftman |
| 5,738,852 A | 4/1998 | Robinson et al. |
| 6,408,853 B1 | 6/2002 | Chang |
| 6,631,718 B1 | 10/2003 | Lovell |
| 6,834,650 B1 | 12/2004 | Fini et al. |
| 7,243,652 B2 * | 7/2007 | Chang ..................... 128/206.26 |
| 2005/0199239 A1 | 9/2005 | Lang et al. |

OTHER PUBLICATIONS

PCT Search Report and Written Opinion, Oct. 5, 2007.

* cited by examiner

*Primary Examiner* — Patricia Bianco
*Assistant Examiner* — Camtu Nguyen
(74) *Attorney, Agent, or Firm* — Michael W. Haas

(57) ABSTRACT

A respiratory mask including a base plate adapted for connection to a gas source and a bladder secured to the base plate to form a generally fluid tight seal with the base plate, and defining at least one internal chamber with the base plate for receiving a fluidizing medium to fill the bladder and form a resilient cushion.

16 Claims, 30 Drawing Sheets

RESPIRATORY MASK

CROSS-REFERENCE TO RELATED APPLICATIONS

This application claims priority under 35 U.S.C. §119(e) from provisional U.S. patent application No. 60/736,709 filed Nov. 15, 2005 the contents of which are incorporated herein by reference.

BACKGROUND OF THE INVENTION

1. Field of the Invention

The present invention relates generally to gas flow delivery systems and, more particularly, gas flow delivery systems that utilize a respiratory mask to deliver a gas to a patient.

2. Description of the Related Art

Gas flow delivery systems are used to deliver a flow of gas to an airway of a subject. Examples of gas flow delivery systems in the medical field include a ventilator or respirator, which replaces or supplements a patient's respiration, and a pressure support system, which provides a flow of gas to an airway of a patient at an elevated pressure to treat a medical disorder, such as obstructive sleep apnea (OSA). Pressure support systems include, but are not limited, to continuous positive airway pressure (CPAP) devices, which deliver a constant positive pressure to the airway of a patient over multiple respiratory cycles, and variable pressure devices where the pressure of the flow of gas delivered to the patient is variable.

Variable pressure devices include auto-titrating devices that are capable of changing a base pressure or pressure profile delivered to the patient based on a monitored condition of the patient. Other variable pressure devices change the pressure of the flow of gas during a respiratory cycle. These devices include the following: a proportional assist ventilation (PAV®), a proportional positive airway pressure (PPAP) device, a C-Flex™ device, a Bi-Flex™ device, and a BiPAP® device manufactured and distributed by Respironics, Inc. of Pittsburgh, Pa. The BiPAP® device is a bi-level pressure support system in which the pressure provided to the patient varies with the patient's respiratory cycle so that a higher pressure is delivered during inspiration than during expiration.

A typical gas flow delivery system comprises a pressure/flow generating system that produces a flow of gas for delivery to a patient and a system for communicating the flow of gas to the patient. The latter system typically includes a flexible conduit having one end coupled to the pressure/flow generating device and a second end portion that couples to an airway of the patient through a patient interface. The conduit, which is also referred to as a patient circuit, carries the flow of gas from the pressure generating device during operation of the system. The patient interface device, typically in the form of a nasal, oral, or nasal/oral mask, is coupled to the second end portion of the conduit to communicate the flow of gas from the patient circuit to the airway of the patient.

Patient interfaces utilizing an inflatable contact rim, or cuff, are generally known. In general, such rims are inflated to a desired pressure through the use of pressurizing air but remain resiliently elastic and can, therefore, conform accurately to a wearer's face. In this manner, a desired close contact between the mask and the wearer's face is achieved.

The inflatable rims typically take the form of an "innertube" type inflatable structure. Such inflatable rims are typically manufactured either by the folding of a unitary film or by a blow molding or "slush" molding process. Typically, no matter which process is used to form the inflatable rim, special measures (e.g., gluing or welding) are necessary for the circumferential closure of the resulting molded material, so that an isolated interior space is formed. A special closure device must be provided (see, for example, U.S. Pat. No. 3,695,264) so that the air remains in this interior space after inflating the rim, and this also increases the total cost of the mask. Finally, a further disadvantage is that the resulting mask is not always in a ready-to-use condition because the rim typically first has to be inflated and the closure device has to be actuated.

Respiratory masks having a non-gaseous "filling" substance in the rim, such as a gel or liquid, are known in the art for maintaining the rim in a constant ready-to-use condition, (e.g., held in a taut or resiliently elastic state by the filling substance). However, this type or rim has the same manufacturing disadvantages discussed previously, with only the closure device being eliminated. Finally, non-inflatable rims for respiratory masks have traditionally been manufactured by vulcanization, which is also relatively expensive. Patents disclosing various versions of each of the foregoing types of mask rim configurations are described hereinafter.

U.S. Pat. No. 790,057 discloses an early inhaler anesthesia mask having a generally inward curvature with an adaptation for the bridge of the nose of a patient. U.S. Pat. No. 1,206,045 discloses a nasal inhaler with a hard, gas tight support shell with a "flange" formed of plastic material situated between the shell and the patient as a sealing means. U.S. Pat. No. 2,313,999 generally discloses a double-shelled mask formed from flexible rubber. U.S. Pat. Nos. 2,535,938; 2,625,155; 2,765,788; and 3,042,035 generally disclose masks with a relatively hard material forming the sealing flange of the mask. The downward pressure applied to the masks disclosed by these patents tends to increase the seal between the wearer's face and the flange by causing a reaction of opposing skin and muscles, but with increasing discomfort to the wearer. U.S. Pat. No. 2,875,757 discloses an inflatable cuff type mask with an inflation valve.

U.S. Pat. No. 4,062,357 discloses a modern version of a mask with an inflatable rim. The mask disclosed by this patent includes a faceplate and an air-filled cushion rim attached to the faceplate. U.S. Pat. No. 4,201,205 discloses an oxygen mask with a flexible clear plastic shell having a flange for improving the seal between the mask and the wearer's face. U.S. Pat. No. 4,347,205 discloses an inflatable rim with a dual lumen configuration. U.S. Pat. No. 4,803,981 discloses a nose inhaler having only a firm rubber foam material for engaging the wearer's nose. U.S. Pat. No. 4,807,617 discloses a scavenging mask that cooperates with a mask having an inflatable rim. U.S. Pat. No. 4,913,401 discloses a valve assembly generally representative of inflating valves for inflatable rims. U.S. Pat. No. 4,971,051 discloses a CPAP device with an inflatable rim that is inflated under air pressure provided by a balloon.

U.S. Design Pat. No. D293,613 discloses an inflatable rim type mask with an inflating valve located at the nose bridge area. U.S. Design Pat. No. D323,908 discloses an inflatable rim type mask with an extension of the support shell or base located just superior to the bridge of the nose, for supporting one or more fingers of an anesthesiologist or nurse during use.

U.S. Pat. No. 5,121,745 shows an inflatable rim-type mask adapted specifically for use in CPR applications and which is collapsible to a thin profile when not in use.

U.S. Pat. No. 5,738,094 discloses a mask with an inflatable rim generally including a faceplate with a circumferential rim or flange and an air-fillable rim adhered or otherwise secured to the flange of the faceplate. U.S. Pat. No. 6,408,853 discloses a mask with an inflatable rim generally similar to that disclosed by U.S. Pat. No. 5,738,852, but further discloses a method of forming the inflatable rim so that the rim may have an increased wall thickness on the flange facing side of the rim and a thinner wall thickness on the patient facing side of the rim. Finally, U.S. Pat. No. 6,834,650 discloses a face or nose mask with two annular chambers forming a cushion rim. Each of the chambers is air-inflatable and may be continuously pressurized by an external air source.

In view of the foregoing, a need generally exists for an improved respiratory mask in which the components of the mask are easy to manufacture thereby facilitating assembly of the mask. Additionally, a need exists for a respiratory mask that is easy to don and adjust and is comfortable to the wearer. Further, a specific need exists for a respiratory mask having an inflatable contact rim or cushion that exhibits improved sealing characteristics, is easy to inflate and deflate, and which can establish and maintain desired inflation pressures.

SUMMARY OF THE INVENTION

The respiratory mask of the present invention generally comprises a base plate adapted for connection to a gas source, and a bladder secured to the base plate to form a generally fluid tight seal with the base plate and defining at least one internal chamber with the base plate for receiving a fluidizing medium to fill the bladder and form a resilient cushion. The fluidizing medium may be a gas, such as air, a liquid such as mineral oil or saline solutions as examples, or other materials such as a gel, or any combination of a gas, liquid, or solid medium. If a gas medium is used as the fluidizing medium for the bladder, the respiratory mask will comprise a gas-filled cushion. In such an embodiment, a pressure relief valve associated with the internal chamber may be advantageous to regulate pressure in the internal chamber and limit pressure therein, typically to improve the comfort characteristics for the wearer of the respiratory mask.

Another aspect of the invention relates to a bladder suitable for use with a respiratory mask. The bladder generally comprises a unitary body defining a generally U-shaped transverse cross-section. The bladder body typically comprises a non-uniform wall thickness over the generally U-shaped transverse cross-section thereof. The bladder body may comprise a base portion and a cushion portion defining the generally U-shaped transverse cross-section. The base portion may comprise opposed flanges adapted to associate the bladder with a base plate of the respiratory mask. The base portion may have a wall thickness greater than the cushion portion. The bladder body may be formed to encompass a forehead extension extending from the base plate of the respiratory mask. Additionally, the bladder body may comprise at least one internal divider to define a plurality of internal chambers therein.

Another aspect of the invention relates to a method of assembling a respiratory mask. The assembly method generally comprises providing a base plate adapted for connection to a gas source, providing an expandable bladder adapted to be connected to the base plate, and attaching the bladder to the base plate to form a generally fluid tight seal with the base plate and defining at least one internal chamber with the base plate for receiving a fluidizing medium to fill the bladder and form a resilient cushion.

The step of securing the bladder to the base plate may comprise using a retaining member to secure the bladder to the base plate to form the generally fluid tight seal with the base plate. Additionally, the method may comprise attaching the retaining member to the base plate by mechanically connecting or bonding the retaining member to the base plate. The bladder generally comprises a unitary body defining a generally U-shaped transverse cross-section. The bladder body may comprise a base portion and a cushion portion defining the generally U-shaped transverse cross-section, and the step of attaching the bladder to the base plate may comprise sandwiching at least a portion of the base portion between the retaining member and base plate to form the generally fluid tight seal with the base plate.

In another embodiment, the respiratory mask generally comprises a base plate comprising a track defining a plurality of slots, and a latch device engaged in the track. The latch device may generally comprise a latch body having opposing sides connected by a first connecting member and a second connecting member. The second connection member may define a central opening and be at least partially resiliently deformable. The latch device may further comprise a post member disposed in the central opening and having a first end engaged with the first connecting member and a second end projecting from the central opening and engaged in one of the slots in the track. In operation, when force is applied to at least one of the opposing sides directed towards the post member causes, the second connecting member typically deforms in a direction towards the second end of the post member thereby lifting the second end from engagement with the slot.

The opposing sides may be formed with finger grip surfaces. Additionally, a third connecting member may connect the opposing sides and define a space with the first connecting member for accepting a strap. The second connecting member may comprise a resiliently deformable distal portion defining the central opening. Further, the latch body and post member may be integrally formed, for example, of plastic material, or be formed as separate elements, for example, from plastic material. The second end of the post member may comprise a ball joint. The ball joint may comprise a tab for registering with the slots.

In a further embodiment, the respiratory mask generally comprises a base plate comprising a track defining a plurality of slots, and a latch device engaged in the track. The latch device may generally comprise a latch body having opposing sides connected by a first connecting member and a second connecting member. The second connection member may define a central opening and comprise a resiliently deformable portion contacting the track. The latch device may further comprise a post member disposed in the central opening and having a first end engaged with the first connecting member and a second end projecting from the central opening and engaged in one of the slots in the track. In operation, when force is applied to the latch body, typically in a direction generally aligned or parallel to the post member, the second connecting member typically deforms in a direction towards the first connecting member, thereby projecting the second end of the post member further through the central opening and lifting the second end from engagement with the slot.

In this embodiment, a third connecting member may connect the opposing sides and define a space with the first connecting member for accepting a strap. The second connecting member may comprise a resiliently deformable distal portion defining the central opening. Further, the latch body and post member may be integrally formed, for example, of plastic material, or be formed as separate elements, for example, from plastic material. The second end of the post member may comprise a ball joint. The ball joint may comprise a tab for registering with the slots.

These and other objects, features, and characteristics of the present invention, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention. As used in the specification and in the claims, the singular form of "a", "an", and "the" include plural referents unless the context clearly dictates otherwise.

BRIEF DESCRIPTION OF THE DRAWINGS

FIG. 14b is a partial cross-sectional perspective view of the inflatable rim taken along line 14b-14b of FIG. 14a.

DETAILED DESCRIPTION OF THE EXEMPLARY EMBODIMENTS

Figure 1:
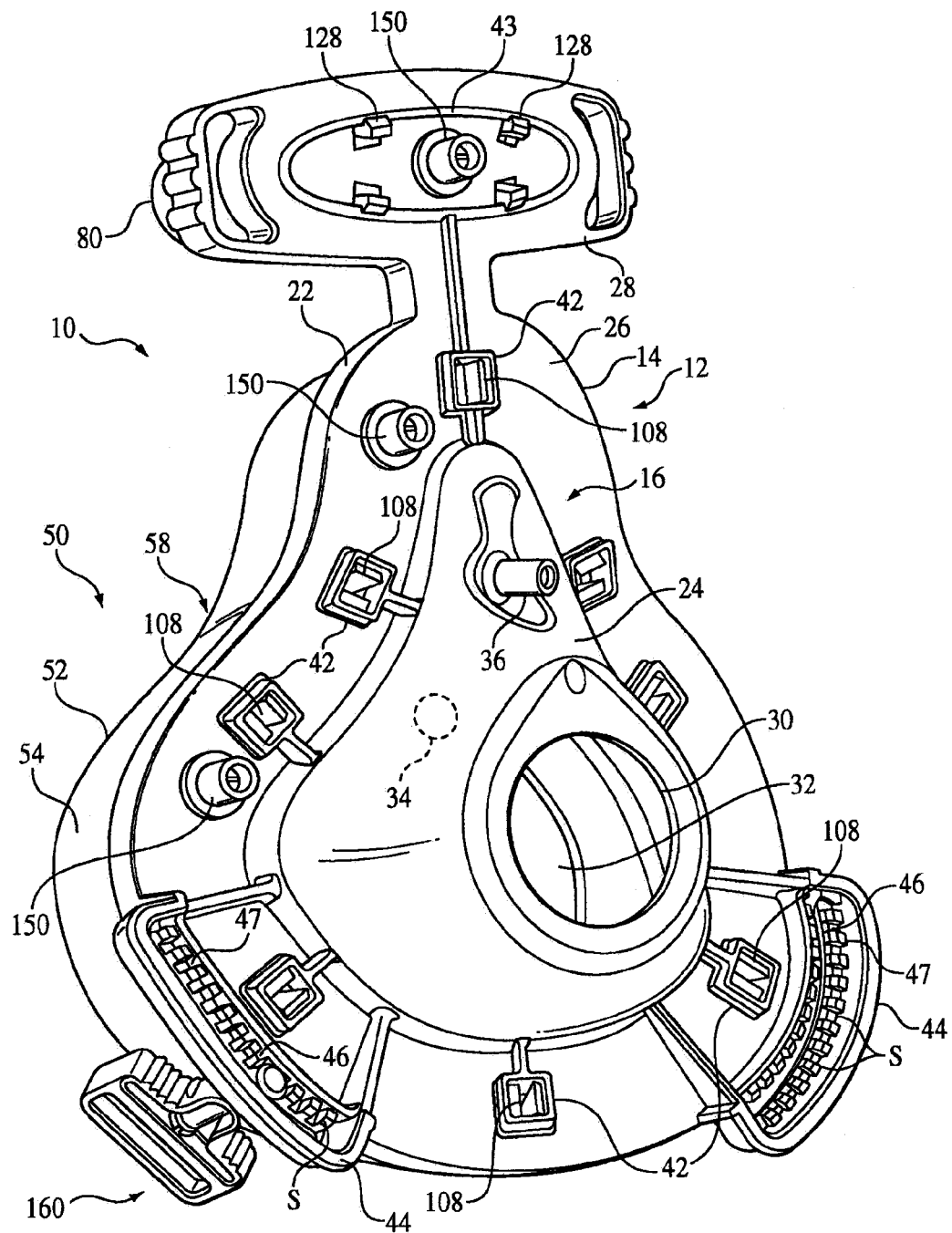
FIG. 1 is a front perspective view of an oral-nasal embodiment of a respiratory mask in accordance with the present invention.
Figure 2:
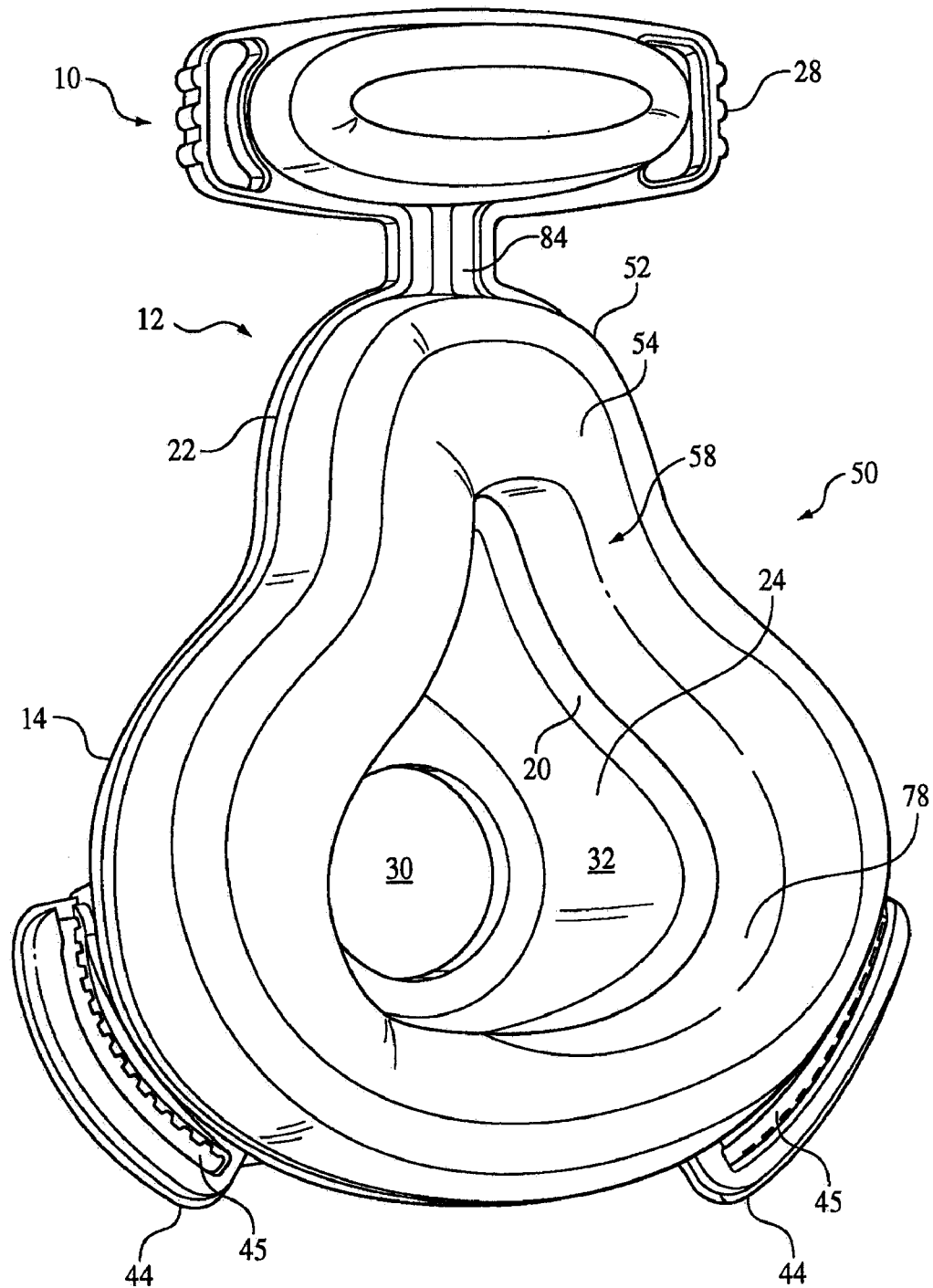
FIG. 2 is a second rear perspective view of the respiratory mask of FIG. 1.
Figure 3:
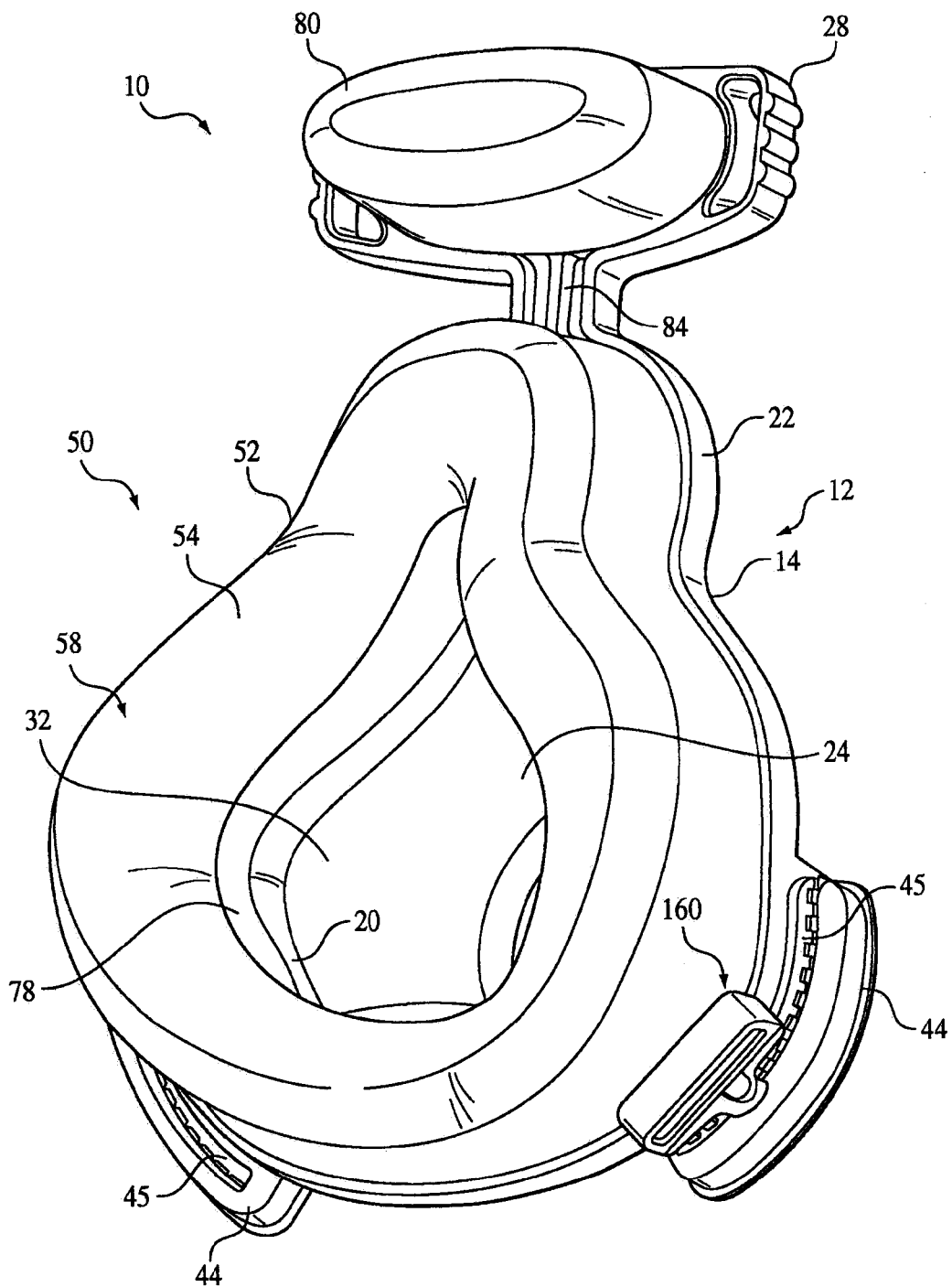
FIG. 3 is a perspective view of the respiratory mask of FIG. 1.

For purposes of the description hereinafter, the words "up", "down", "vertical", "horizontal", "top", "bottom", "forward", "rearward", "distal", "proximal", "inner", "outer", and like orientation terms, if used, shall relate to the embodiment of the invention as it is oriented in the accompanying drawing figures. However, it is to be understood that the present invention may assume many alternative variations and embodiments except where expressly specified to the contrary. It is also to be understood that the specific devices and embodiments illustrated in the accompanying drawing figures and described herein are simply exemplary embodiments of the invention, and wherein like elements are designated with like reference numerals throughout.

Referring to FIGS. 1-10, an embodiment of a respiratory mask 10 in accordance with the present invention is shown. Respiratory mask 10 is generally sized and shaped to cover a wearer's mouth and nose for covering the wearer's airway passages, and may be described as an oral-nasal respiratory mask. Other embodiments described in this disclosure are adapted as nasal masks only, generally sized and shaped to cover a wearer's nose and the wearer's nasal airway passages. Additionally, it is within the scope of the present invention to configure respiratory mask 10 for covering only the wearer's mouth if desired. Respiratory mask 10 may be used in medical applications or procedures such as for delivering airflows containing anesthetic or an oxygen supply to a patient, or be associated with specialized medical treatment devices such as Continuous Positive Air Pressure (CPAP) devices used to treat sleep disorders such as sleep apnea. Generally, respiratory mask 10 comprises a generally rigid support or base structure 12 and an inflatable rim or cushion 50 associated with base structure 12. Typically, inflatable rim 50 is attached to base structure 12 by a retaining member 100 that establishes a generally fluid tight seal between inflatable rim 50 and base structure 12.

Base structure 12 provides a generally rigid structure for supporting inflatable rim 50. Inflatable rim 50 is typically mechanically affixed to base structure 12 by retaining member 100 but may also be secured to base structure 12 by other means, such as by permanent bonding of retaining member 100 to base structure 12. Examples of such permanent bonding techniques include, but are not limited to, ultrasonic welding or chemical fusing of retaining member 100 to base structure 12. Base structure 12 is a generally rigid structure but is intended to allow some resilient flexure. Base structure 12 defines the general oral-nasal covering shape of respiratory mask 10 and is adapted to interface with external devices such as a hose or conduit for associating respiratory mask 10 with an airflow supply containing anesthetic, an oxygen supply, a CPAP device, and like applications.

Base structure 12 is generally formed by a base plate 14, which is typically a unitary member formed generally in the shape of a faceplate that is sized and shaped to cover a wearer's mouth and nose (e.g. oral-nasal airway passages). Base plate 14 has an outward facing or external side 16 and an internal side 18 to which inflatable rim 50 is secured. Internal side 18 is typically formed with inner and outer circumferentially or perimetrically-extending lips or rims 20, 22 which project outward from internal side 18 and act as inner and outer walls to restrain the inner and outer base areas of inflatable rim 50 as detailed herein.

Base plate 14 is formed with a bulbous mouth and nose covering portion or area 24, referred to hereinafter simply as "covering portion 24." Covering portion 24 projects outward on external side 16 of base plate 14 and is generally sized and configured to accept and cover at least the wearer's mouth and nose. Base plate 14 is further formed with a circumferential or perimetrically-extending attachment flange 26 provided radially outward from covering portion 24. Inflatable rim 50 is intended to be attached and secured to attachment flange 26 on the internal side 18 of base plate 14 in such a manner as to provide a generally fluid tight seal between inflatable rim 50 and attachment flange 26. Inner and outer rims 20, 22 generally define the inner and outer boundaries of attachment flange 26 on the internal side 18 of base plate 14. Attachment flange 26 provides the specific support structure for inflatable rim 50.

As stated previously, base plate 14 is typically a unitary member and typically has covering portion 24 and attachment flange 26 formed integrally together, for example, during a plastic molding process. However, if desired, covering portion 24 and attachment flange 26 may be separate elements that are joined together by customary means in the medical mask field to form base plate 14. Base plate 14 is typically formed or molded from plastic material, such as polycarbonate or other similar rigid or semi-rigid plastic, but possibly could be constructed of metal such as aluminum or a suitable medical grade stainless steel.

Base plate 14 may optionally include a forehead extension 28 extending from a top end of attachment flange 26. Typically, forehead extension 28 is formed integrally as part of base plate 14 as illustrated, but may be provided as a separate structure that is attached to base plate 14 and attachment flange 26 in particular. Forehead extension 28 is adapted to support an inflatable forehead cushion 80 in much the same manner as attachment flange 26 supports a main body area or portion of inflatable rim 50. As described further herein, inflatable rim 50 is typically a unitary structure or member having forehead cushion 80 formed as part of inflatable rim 50. However, since forehead cushion 80 may easily be provided as a separate structure from the main body area of portion of inflatable rim 50, distinct reference numerals are used in this disclosure to identify the elements associated with forehead cushion 80 and the support structure therefore on base plate 14. Accordingly, for the purposes of this disclosure, the term "inflatable rim" is generally intended to include forehead cushion 80 even though this element is separately designated by reference numeral "80."

Likewise, forehead extension 28 is generally intended to be considered as part of attachment flange 26 even though forehead extension 28 may be a distinct structure that is attached to attachment flange 26 by suitable means such as mechanical fasteners and the like. Forehead cushion 80 is secured to forehead extension 28 to provide a generally fluid tight seal between forehead cushion 80 and forehead extension 28 in a similar manner to the connection between the main body portion of inflatable rim 50 and attachment flange 26. In particular, forehead cushion 80 is typically secured to forehead extension 28 by a forehead retaining member 120 in much the same manner as the main body portion of inflatable rim 50 is secured to attachment flange 26 by retaining member 100. Specific details of retaining member 100 and forehead retaining member 120 are provided herein.

Outer rim 22 on attachment flange 26 typically also extends around the outer periphery of forehead extension 28 to form an outer peripheral wall or rim on forehead extension 28 to restrain the outer base area, or portion, of forehead cushion 80 when attached to forehead extension 28. Accordingly, outer rim 22 is generally continuous around the entire periphery of base plate 14. However, outer rim 22 is formed to leave an open connecting passageway 29 between attachment flange 26 and forehead extension 28 for a connecting member or structure generally connecting the main body portion of inflatable rim 50 and forehead cushion 80 as described herein.

Figure 26:
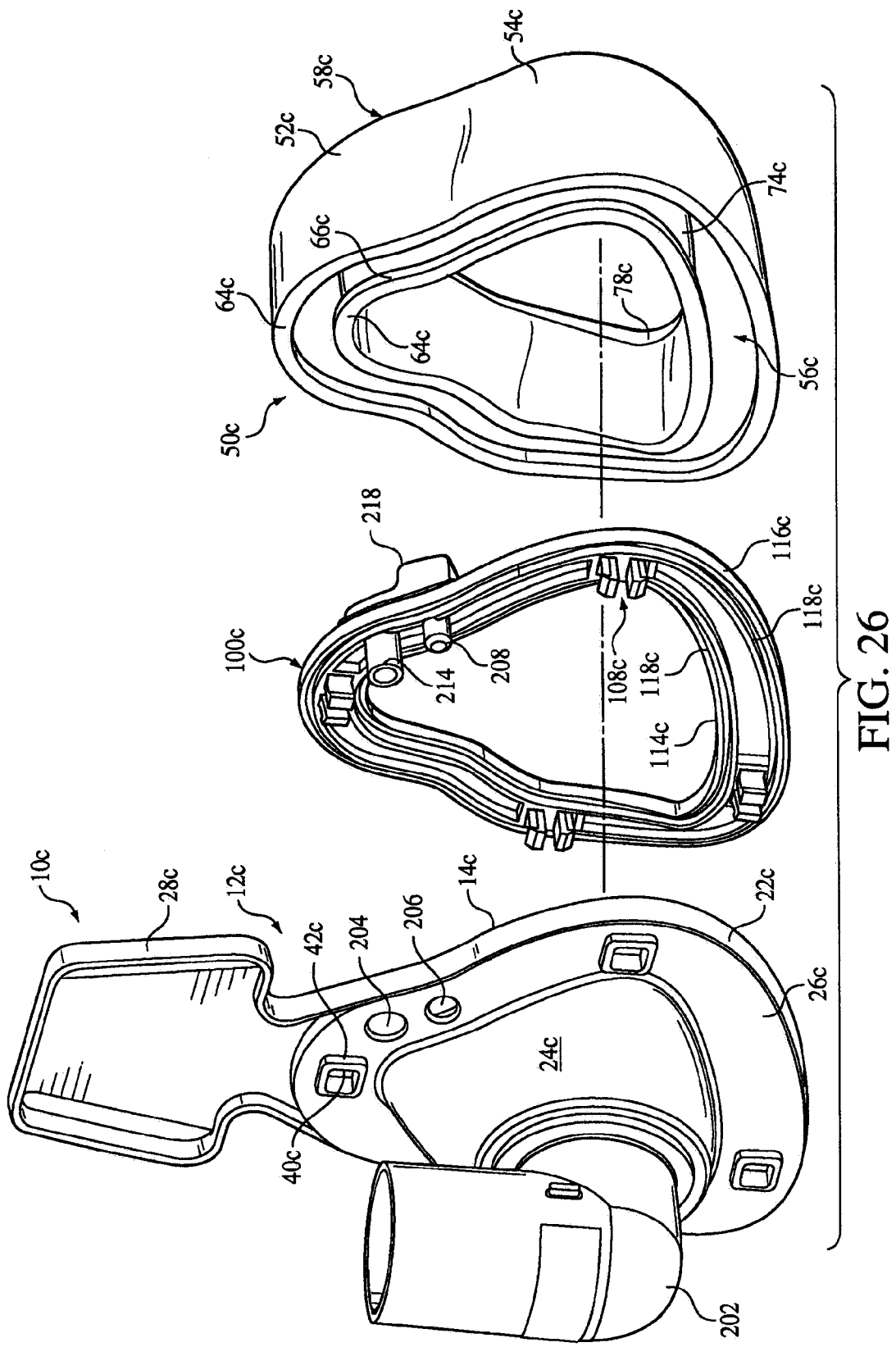
FIG. 26 is an exploded perspective of the respiratory mask of FIG. 21 viewed from an opposite end of the view in FIG. 23 and with an attached inflation/deflation valve.
Figure 27:
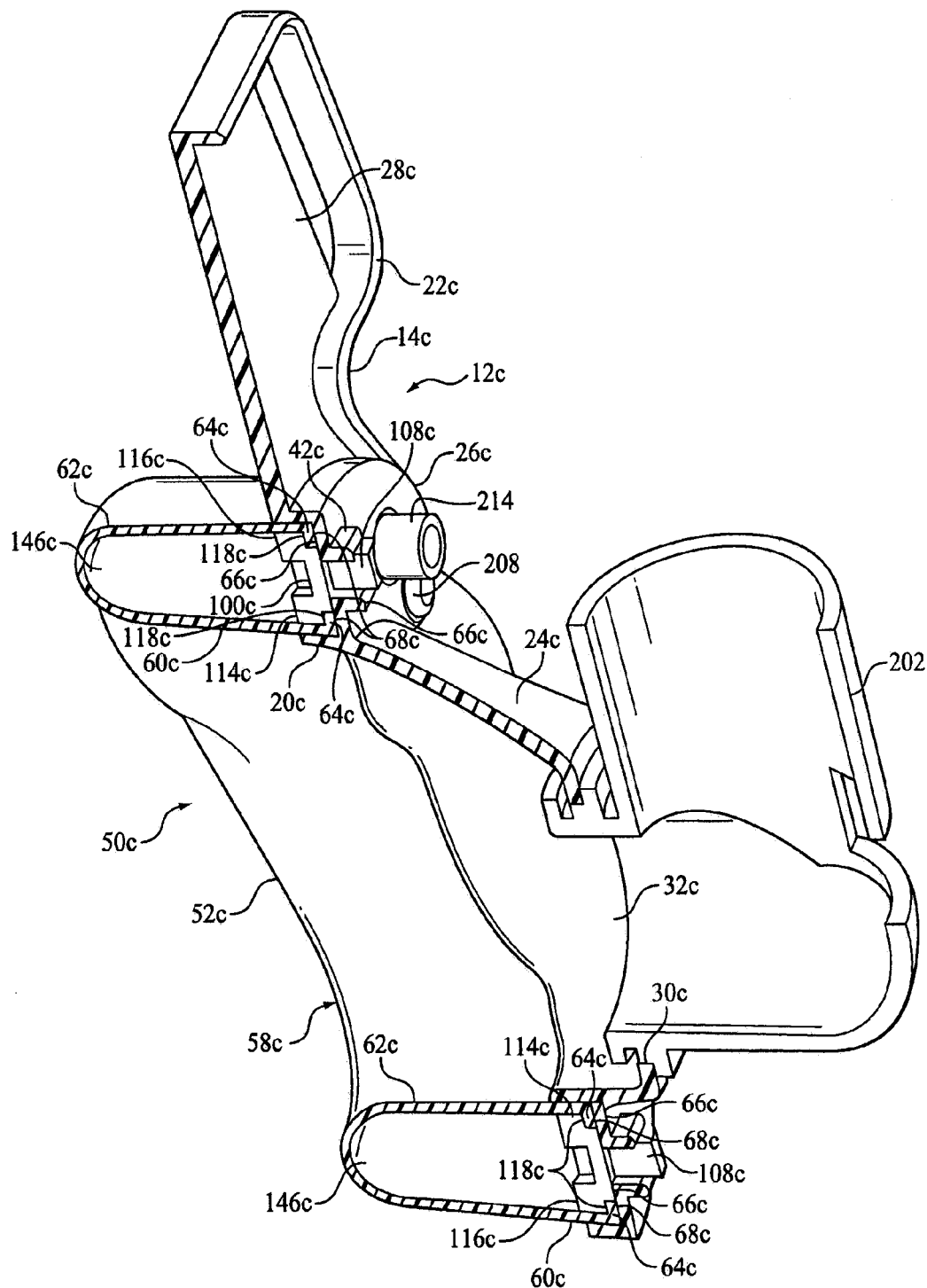
FIG. 27 is a generally longitudinal cross-sectional view of the respiratory mask of FIG. 21 taken along line 27-27 in FIG. 22.
Figure 28:
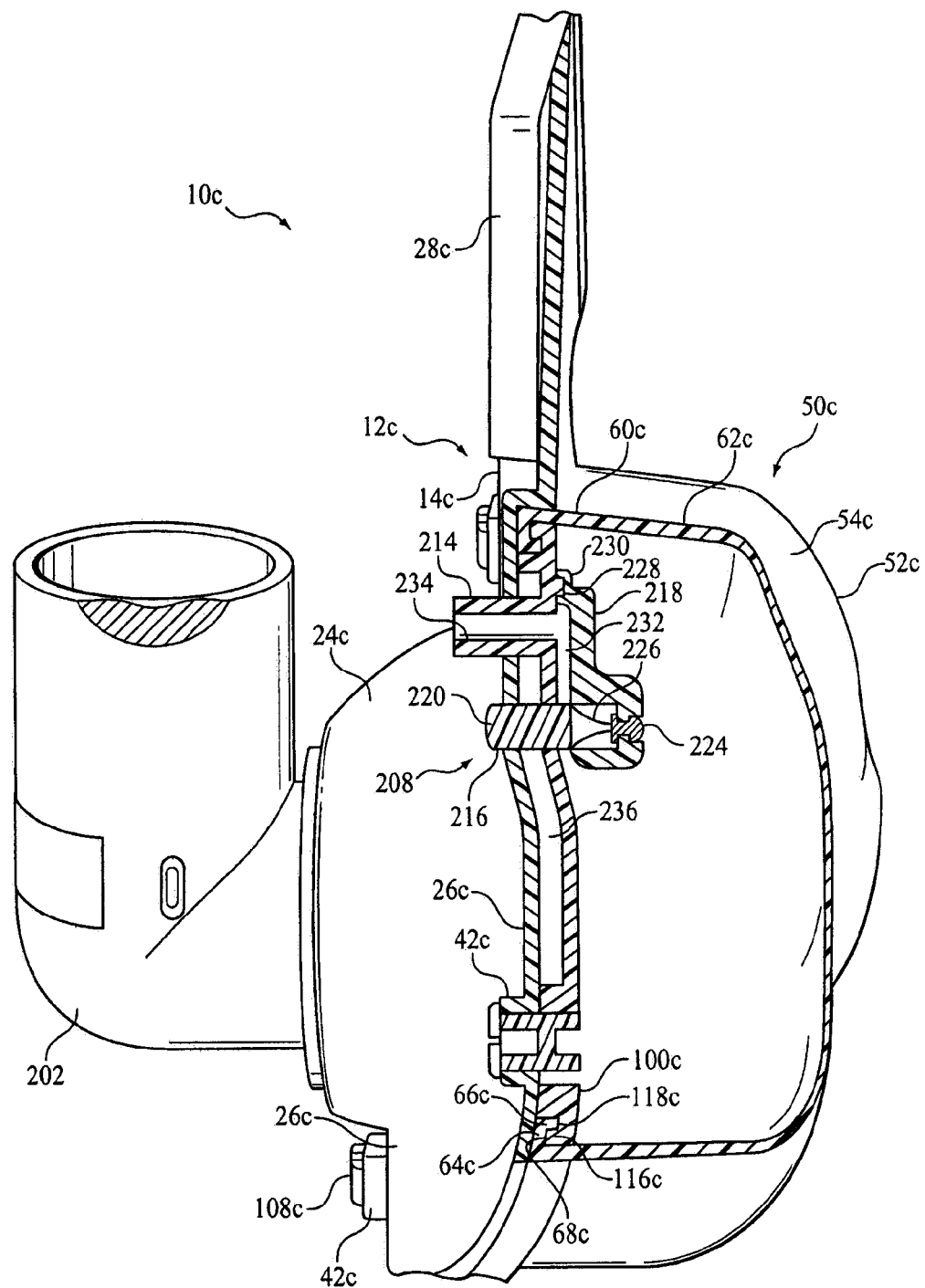
FIG. 28 is a side and partial cross-sectional view of the respiratory mask of FIG. 21.

Covering portion 24 is typically formed with a large central opening 30. Central opening 30 may be formed in covering portion 24 during a molding process forming base plate 14 or, alternatively, may be cut into covering portion 24 after the molding of base plate 14 is complete. Central opening 30 is provided as the main interface location or adaptation point for associating respiratory mask 10 with other devices. Accordingly, central opening 30 may be adapted to connect to a supply conduit for supplying airflows containing anesthetic or to an oxygen supply conduit to respiratory mask 10, or to a positive air pressure supply conduit associated with a CPAP device. Additionally, central opening 30 may be adapted to accept a fixture used to connect to a supply conduit from an external device. An example of such a fixture is a 90° elbow as best appreciated with reference to FIG. 26 discussed herein.

Covering portion 24 generally defines a substantially concave internal cavity or recess 32 in internal side 18 of base plate 14 that is shaped to conform to the oral-nasal shape of the human face. Concave recess 32 is generally shaped to receive a wearer's nose and mouth with attachment flange 26 defining an outer periphery around the concave recess 32. Accordingly, with the main body portion of inflatable rim 50 secured or otherwise attached to attachment flange 26 on the internal side 18 of base plate 14, inflatable rim 50 is generally adapted to contact and engage the wearer's face along a continuous perimeter generally encompassing the bridge of the nose, extending along the wearer's cheeks, and extending below the wearer's lower lips. Covering portion 24 may be formed with one or more utility openings 34 for interfacing with other apparatus that may be used with respiratory mask 10. Utility opening 34, shown in dotted lines, is an optional opening for accepting a feeding tube or like device. Further, covering portion 24 may be formed with a projecting conduit 36 for providing fluid communication between concave recess 32 and an external device. Conduit 36 typically serves as a pressure pick-up port for pressure feedback to associated devices or for monitoring purposes.

As indicated, attachment flange 26 extends peripherally about covering portion 24 and provides support for inflatable rim 50. As described herein, inflatable rim 50 in one embodiment may be divided into separate inflation "chambers" or "pockets" each of which may be separately filled with a fluidizing medium to inflate or fill inflatable rim 50. As a result, attachment flange 26 typically defines at least one inflation/deflation opening 38 for each chamber/pocket formed in inflatable rim 50. Inflation/deflation openings 38 are adapted to receiving a device or structure, such as a valve, used to admit the fluidizing medium into the chambers/pockets and, typically, for withdrawing the fluidizing medium from the chambers/pockets. Hereinafter, inflation/deflation openings 38 will be referred to simply as "inflation openings 38" but it should be clear that these openings may also have a deflation or fluidizing medium "removal" function as well.

Additionally, attachment flange 26 typically defines one or more tab receiving openings 40 for receiving mechanical tabs, as discussed herein, associated with retaining rim 100 used to secure inflatable rim 50 to base plate 14 and attachment flange 26 in particular. As described herein, retaining member 100 typically includes a plurality of mechanical attachment tabs adapted to engage tab openings 40 to secure at least portions of inflatable rim 50 in a compressed condition between retaining member 100 and attachment flange 26. However, it is envisioned that the mechanical engagement between retaining member 100 and attachment flange 26 could be replaced by a permanent bonding technique, as indicated previously. Tab openings 40 typically include a raised tab rim 42 on the external side 16 of base plate 14 that surround and protect the mechanical tabs. Several tab openings 40 are also defined in forehead extension 18 for accepting mechanical tabs associated with forehead retaining member 120. Forehead retaining member 120, as discussed herein, includes mechanical tab structures generally similar to those found on retaining member 100. The engagement of these mechanical tab structures in tab openings 40 in forehead extension 28 is used to secure forehead cushion 80 to forehead extension 28 in a generally fluid-tight manner, as described herein. External side 16 of base plate 14 and, correspondingly, the external side of forehead extension 28 typically defines a generally oval-shaped raised lip or rim 43 forming a rim or lip structure for engagement by the mechanical tabs associated with forehead retaining member 120, as fully detailed herein.

Base plate 14 and, more particularly, attachment flange 26 typically includes attachment structure for securing attachment straps (not shown) to respiratory mask 10. Such straps are used to secure respiratory mask 10 to a wearer's face. Typically, the straps extend around the wearer's head and are joined, for example, by a hook-and-loop fastener. Alternatively, a single elastic strap having its ends secured to opposite sides of base plate 14 may be used to secure respiratory mask 10 to a wearer's face. The strap attachment structure on base plate 14 is comprised of a pair of tracks 44 disposed on opposite lower sides of base plate 14 and extending outward from the external side 16 of base plate 14. Tracks 44 are typically formed as part of attachment flange 26 on the external side 16 of base plate 14. Tracks 44 are generally arcuate shaped structures which are typically integrally formed as part of base plate 14, for example during a molding process. Tracks 44 are used to support respective latches 160 adapted to receive and support respective fastening straps, or opposite ends of a single fastening strap. Tracks 44 are typically formed with an elongated and arcuate adjustment slot 45 (shown in FIG. 16) comprising a plurality of engagement slots 46 disposed on opposing sides thereof for receiving projecting structure on latches 160 used to secure latches 160 in a fixed but releasable position in tracks 44. Engagement slots 46 are defined between a plurality of contact elements 47 each having a tapered or curved (e.g., arcuate) face S facing adjustment slot 45. Tracks 44 are disposed generally along the lower lateral sides of base plate 14 so that the straps associated with latches 160 may extend around the wearer's head along the wearer's left and right lower cheek areas.

Finally, forehead extension 28 includes a separate inflation/deflation opening 48 that is typically identical to inflation openings 38 described previously. Inflation/deflation opening 48 is adapted to support a valve or like structure used to inflate an inflation "chamber" or "pocket" associated with forehead cushion 80 as described herein. Inflation opening 48 will also have a deflation or fluidizing medium "removal" function and is generally referred to herein as "inflation opening 48" to be consistent with "inflation openings 38" described previously.

Generally, inflatable rim 50 is secured, or otherwise attached, to base structure 12 such that a generally fluid tight seal is established between inflatable rim 50 and base structure 12 and, more specifically, between inflatable rim 50 and attachment flange 26 of base plate 14. Inflatable rim 50 generally comprises a unitary, bladder-like structure or member 52, hereinafter referred to simply as "bladder 52" for convenience, and which forms both a main body portion 54 and the forehead cushion 80 of inflatable rim 50. As indicated previously, the term "inflatable rim" is intended to encompass both main body portion 54 adapted to be connected by retaining member 100 to attachment flange 26 and forehead cushion 80 adapted to be connected by forehead retaining member 120 to forehead extension 28. Bladder 52 is typically injection molded in an injection mold from a material that, when solidified, has resiliently elastic properties so that bladder 52 may expand when a fluidizing medium is introduced into bladder 52. When formed, bladder 52 is a unitary structure or body formed or defined by a thin membrane of material. Examples of suitable materials for injection molding bladder 52 include silicone, thermal plastic elastomer, polyurethane, vulcanized rubber and other similar materials.

Bladder 52 is generally formed with an engagement side 56 which is intended for association with retaining member 100 and forehead retaining member 120 and a cushion side 58 which is outward facing and is the side of bladder 52 that forms the contact surface for contacting a wearer's face. A generally transverse cross-section through a section of main body portion 54 and a similar cross-section through a section of forehead cushion 80 of bladder 52 reveals that main body portion 54 and forehead cushion 80 are each generally U-shaped in transverse cross-section. The U-shaped cross section of main body portion 54 is generally defined by a base portion or area 60 having structure adapted for engagement with retaining member 100, and a cushion portion or area 62 which forms the major surface area of the cushion side 58 of bladder 52. Base portion 60 forms approximately the bottom one-third to bottom one-half of the U-shaped cross-section of main body portion 54. Base portion 60 is typically formed with two inward-projecting and generally U-shaped flanges 64. Flanges 64 each comprise an upward extending or upstanding lip or rim 66 which define a groove 68 for engaging a corresponding lip structure on retaining member 100 as described herein.

As will be understood from viewing the various cross-sectional views of bladder 52 in the Figures, the U-shaped cross-sectional forms of main body portion 54 and forehead cushion 80 typically exhibit a non-uniform wall thickness. Base portion 60 of main body portion 54 has a generally thicker wall thickness than cushion portion 62. Since bladder 52 is formed as a unitary member from a thin membrane of material, there is no specific dividing line between base portion 60 and cushion portion 62. However, as suggested, base portion 60 may be considered to form about one-third to one-half of the U-shaped cross-section of main body portion 54. The wall thickness of the membrane forming bladder 52 generally tapers or narrows from base portion 60 to form cushion portion 62 in main body portion 54, and this tapering transition area of wall thickness is identified in the Figures with reference numeral 70.

The non-uniform wall thickness of bladder 52 provides several advantages. The non-uniform wall thickness of bladder 52 allows the base portion 60 and cushion portion 62 of main body portion 54 to expand at different rates to control inflation of inflatable rim 50 when a fluidizing medium is introduced into inflatable rim 50. More specifically, the variable, non-uniform wall thickness of bladder 52 controls the amount and direction of expansion of inflatable rim 50, with more expansion occurring at cushion portion 62 and less expansion occurring at the base portion 60 of main body portion 54 of bladder 52 when the fluidizing medium is introduced into inflatable rim 50. This allows the cushion side 58 of inflatable rim 50 to expand more than the engagement side 56, and the cushion side 58 will readily conform to the shape of the wearer's face. In general, the variable expansion characteristics of bladder 52 enable inflatable rim 50 to expand and shape to a wearer's face to form an effective seal. Thus, the variable expansion characteristics of bladder 52 improve sealing of respiratory mask 10 against the wearer's skin and improve the sealing characteristics of respiratory mask 10 around the wearer's nose and mouth.

Moreover, bladder 52 may include one or more internal walls or dividers 72 in main body portion 54 so that the bladder 52 defines a plurality of internal pockets 72 in main body portion 54 between the internal dividers 72. Internal dividers 72 separate or divide bladder 52 into several individual segments, which may be individually filled with fluidizing medium. The dividers permit dissimilar fluidizing medium to be used in different segments. For instance, it may be advantageous to provide a more resilient region in one segment and a more flexible region in another segment. This may be achieved by varying the pressure in each segment or by utilizing fluidizing medium with differing mechanical properties. Alternatively, internal dividers 72 may comprise pressure equalizing structure 76, such as small holes or perforations or restriction valves, for providing fluid communication between internal pockets or segments 74. Such pressure equalizing structure 76 also allows fluidizing medium to pass from one internal pocket 74 to the next internal pocket 74 when the fluidizing medium is introduced into bladder 52. Accordingly, when the pressure equalizing structures 76 are omitted the respective internal pockets 74 will be isolated from one another and, bladder 52 is joined with retaining member 100 and the retaining member 100 is attached to attachment flange 26, the various, now "enclosed" internal pockets 74 may be pressurized to different levels if desired.

Further, bladder 52 typically includes a sealing flap 78 which is typically integrally formed as part of main body portion 54 during the injection molding process of bladder 52. Sealing flap 78 is generally in the form of a thin membrane of material that extends from cushion portion 62 toward concave recess 32 defined by covering portion 24 of base plate 14. Sealing flap 78 is typically perimetrically-extending around cushion portion 62 on main body portion 54 of bladder 52, and contacts the skin of the wearer typically around bridge of the wearer's nose, along the sides of the nose, and around the wearer's mouth for improving the sealing characteristics of respiratory mask 10. Sealing flap 78 is an optional structure provided on bladder 52.

As indicated previously, forehead extension 28, forehead cushion 80, and forehead retaining member 120 are typically optional components of respiratory mask 10. These components are primarily provided to increase the comfort level for a wearer of respiratory mask 10 and may be omitted. As also indicated previously, these components may easily be provided as separate structures, with forehead extension 28 attached or connected to attachment flange 26 and an independent forehead cushion 80 thereafter secured or attached to forehead extension by forehead retaining member 120. Accordingly, as indicated previously, the features of forehead extension 28 and forehead cushion 80 are designated with distinct reference numerals in this disclosure because theses elements may easily be provided as a separate structures from attachment flange 26 and main body portion 54 of bladder 52, respectively.

Forehead cushion 80 defines a distinct and separate forehead internal pocket 82 from main body portion 54 of bladder 52. Forehead internal pocket 82 is generally similar in structure to internal pockets or segments 74 described previously, but is shaped to match the generally oval shape of forehead extension 28 extending from attachment flange 26 of base plate 14. Forehead cushion 80 is typically connected to main body portion 54 of bladder 52 by a thin, non-inflatable connecting member 84. Forehead cushion 80 includes similar engagement structure for engaging forehead retaining member 120 as that provided on main body portion 54 to engage retaining member 100. In particular, such engagement structure is generally analogous to that provided on base portion 60 of main body portion 54. Forehead cushion 80 thus typically comprises a forehead base portion 88 and a forehead cushion portion or area 90 which are generally analogous to base portion 60 and cushion portion 62 on main body portion 54 described previously. Again, forehead base portion 88 forms approximately the bottom one-third to bottom one-half of the U-shaped cross-section of forehead cushion 80. However, forehead base portion 88 comprises a single, inward-projecting, circumferentially-extending, and generally U-shaped flange 92. Flange 92 comprises an upward extending or upstanding lip or rim 94 which defines a groove 96 for engaging a corresponding lip structure on forehead retaining member 120 as described herein.

As indicated previously, forehead cushion 80 comprises a similar U-shaped transverse cross section as that exhibited by main body portion 54, and further exhibits a similar non-uniform wall thickness associated with forehead base portion 88 and forehead cushion portion 90. As with base portion 60 and cushion portion 62 described previously, forehead base portion 88 has a generally thicker wall thickness than forehead cushion portion 90. The wall thickness of forehead base portion 88 generally tapers or narrows to form forehead cushion portion 90, with forehead base portion 88 and forehead cushion portion 90 connected by a transition area 98 of tapering or narrowing wall thickness. Thus, forehead cushion 80 will have analogous expansion properties to those detailed previously in connection with main body portion 54 of bladder 52.

In the present embodiment of respiratory mask 10, retaining member 100 is illustrated as a multi-piece structure and, in particular, a two-piece structure. Retaining member 100 is typically segmented to correspond to the number of internal pockets 74 formed in bladder 52. Retaining member 100 generally comprises a first retaining member 102 and a second retaining member 104 to correspond to the two internal pockets 74 defined by internal dividers 72 in bladder 52 shown in FIGS. 1-10. Bladder 52 may be further segmented with additional internal dividers 72, and retaining member 100 may be further divided to correspond to the number of additional internal pockets 74 formed in bladder 52 as desired. The first and second retaining members 102, 104 each define an inflation/deflation opening 106 generally formed to coincide with inflation openings 38 in attachment flange 26 of base plate 14. Corresponding or coinciding inflation openings 38, 106 are typically adapted to cooperatively support an inflation/deflation valve as described herein. Inflation/deflation openings 106 will also be referred to herein generally as "inflation openings 106" to conform with the terminology used in connection with inflation openings 38.

The first and second retaining members 102, 104 each further comprise a plurality of attachment tabs 108 extending from a bottom side thereof and which are adapted to engage corresponding tab openings 40 in attachment flange 26 of base plate 14 to secure the first and second retaining members 102, 104 to attachment flange 26. Attachment tabs 108 may come in any suitable for form, but are depicted as generally arrow-shaped tabs as a desirable embodiment for attachment tabs 108. Attachment tabs 108 are each typically formed by a pair of prong members 110 each having a half-arrow shaped head 112. In use, prongs 110 are adapted to flex toward one another as the attachment tabs 108 are inserted into tab openings 40 and then resiliently flex outward to engage the raised rim 42 extending around the respective tab openings 40. As prongs 110 resilient flex outward, prong heads 112 will engage the raised rims 42 around the respective tab openings 40 and thereafter prevent removal of attachment tab 108 from tab openings 40.

Figure 13A:
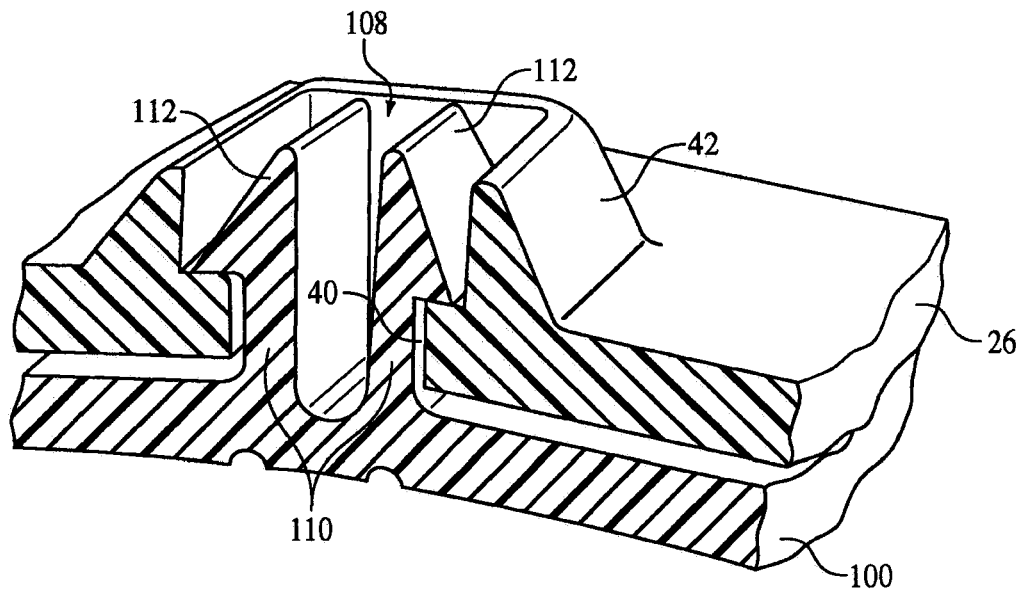
FIG. 13A is a perspective and partial cross-sectional view showing a mechanical attachment mechanism between a base plate and retaining member of the respiratory mask of FIG. 1.
Figure 13B:
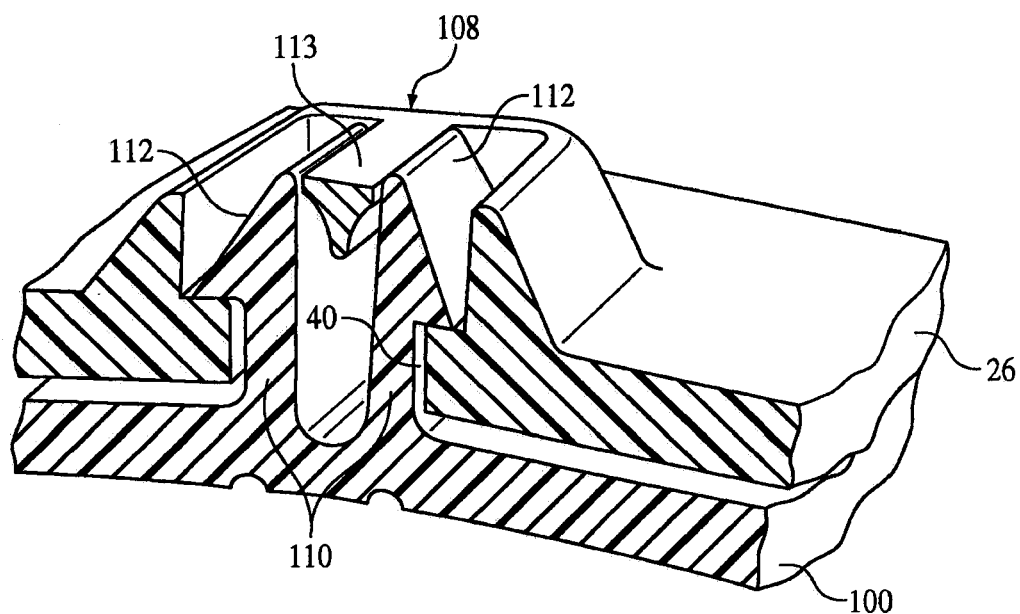
FIG. 13B is a perspective and partial cross-sectional view showing an alternative embodiment of the mechanical mechanism.

Referring briefly to FIGS. 13A and 13B, several modifications to the engagement between attachment tabs 108 on retaining member 100 and tab openings 40 in attachment flange 26 of base plate 14 are illustrated. As FIGS. 13A and 13B illustrate, raised rim 42 around each tab opening 40 may be spaced outward from the periphery of the tab opening 40. When connected, the half-arrow shaped prong heads 112 on prongs 110 may engage only the periphery of tab openings 40 rather than raised rims 42. Raised rims 42, in this configuration, act as protective barriers around the engagement of prong heads 112 with the peripheries of tab openings 40, thereby preventing tampering with this engagement. If desired, raised rims 42 may each be formed with a central cross member 113. Cross members 113 are positioned substantially between the prong heads 112 of prongs 110 when the prong heads 112 are engaged with the peripheries of tab openings 40. As a result, once attachment tabs 108 are inserted through tab openings 40 and prong heads 112 are engage with the peripheries of tab openings 40, cross members 113 prevent prong heads 112 from being deflected or flexed towards one another, thereby prevent removal of attachment tabs 108 from tab openings 40. Cross members 113 provide another structure that prevents tampering with the engagement between prong heads 112 and the peripheries of tab openings 40 once this engagement is established.

Referring again to FIGS. 1-10, first and second retaining members 102, 104 each further define peripheral inner and outer lips or rims 114, 116 along their inner and outer edges. Inner and outer lips 114, 116 are intended to register or cooperate with grooves 68 defined by upstanding lips 66 on opposing flanges 64 formed base portion 60 of main body portion 54 of bladder 52. Peripheral inner and outer lips 114, 116 each define a groove 118 for receiving the respective lips 66 on opposing flanges 64 formed base portion 60 of main body portion 54 of bladder 52. The engagement of attachment tabs 108 with peripheral raised rims 42 extending around tab openings 40 generally causes a compressive force to be exerted on opposing flanges 64 formed on base portion 60 of main body portion 54 of bladder 52, to establish a generally fluid tight seal between main body portion 54 of bladder 52 and attachment flange 26. Additional details relating to the registering engagement between attachment tabs 108 and tab openings 40 and the subsequent compressive force applied by retaining member 100 on opposing flanges 64 are provided herein with respect to the assembly process for assembling respiratory mask 10. Retaining member 100 and, more particularly, first and second retaining members 102, 104 may be formed of a rigid plastic material such as polycarbonate. As with base plate 14, retaining member 100 may also be formed of other suitable materials such as aluminum or stainless steel and grades thereof suitable for use in medical components.

Figure 4:
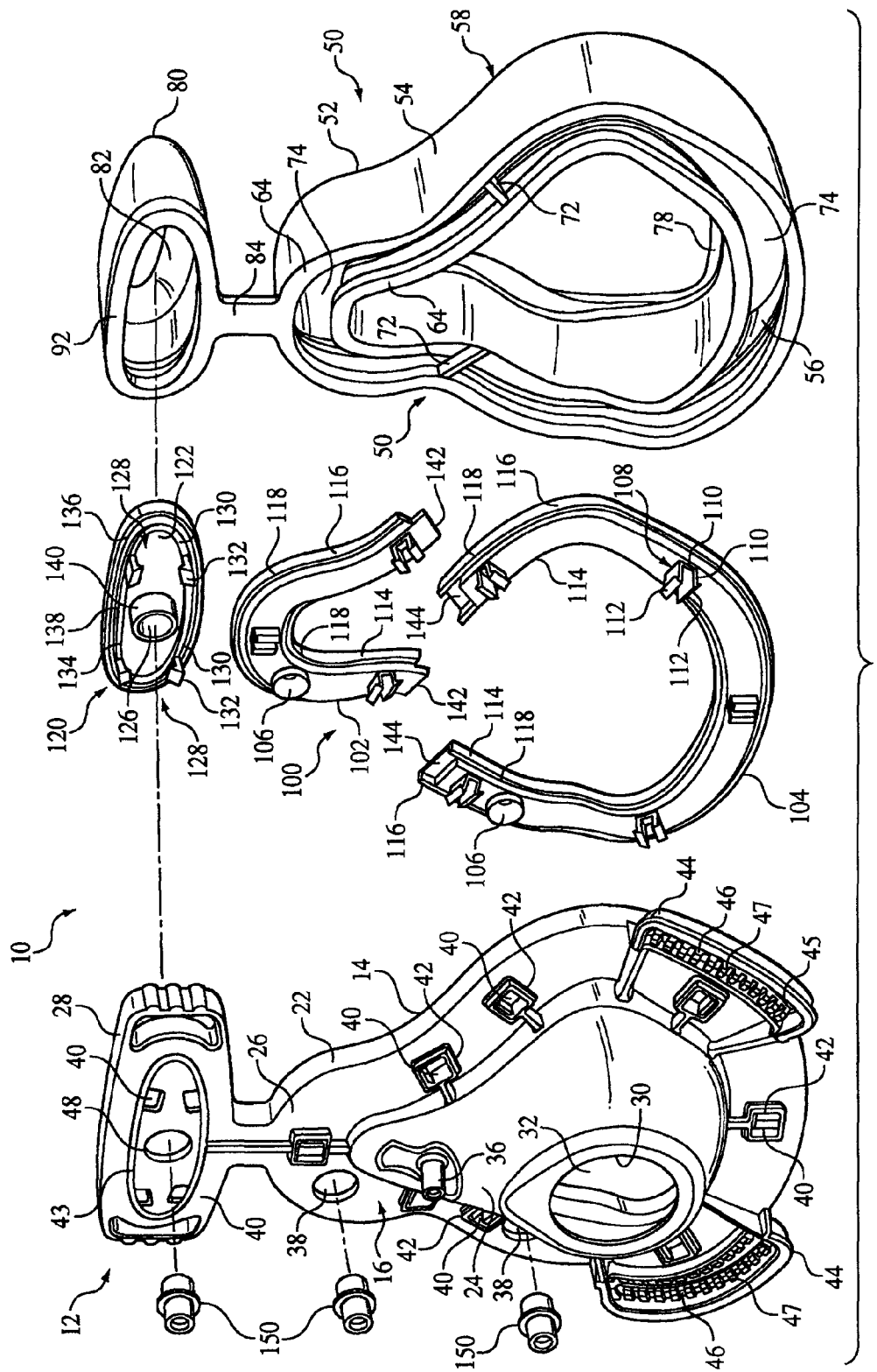
FIG. 4 is an exploded perspective of the respiratory mask of FIG. 1.
Figure 5:
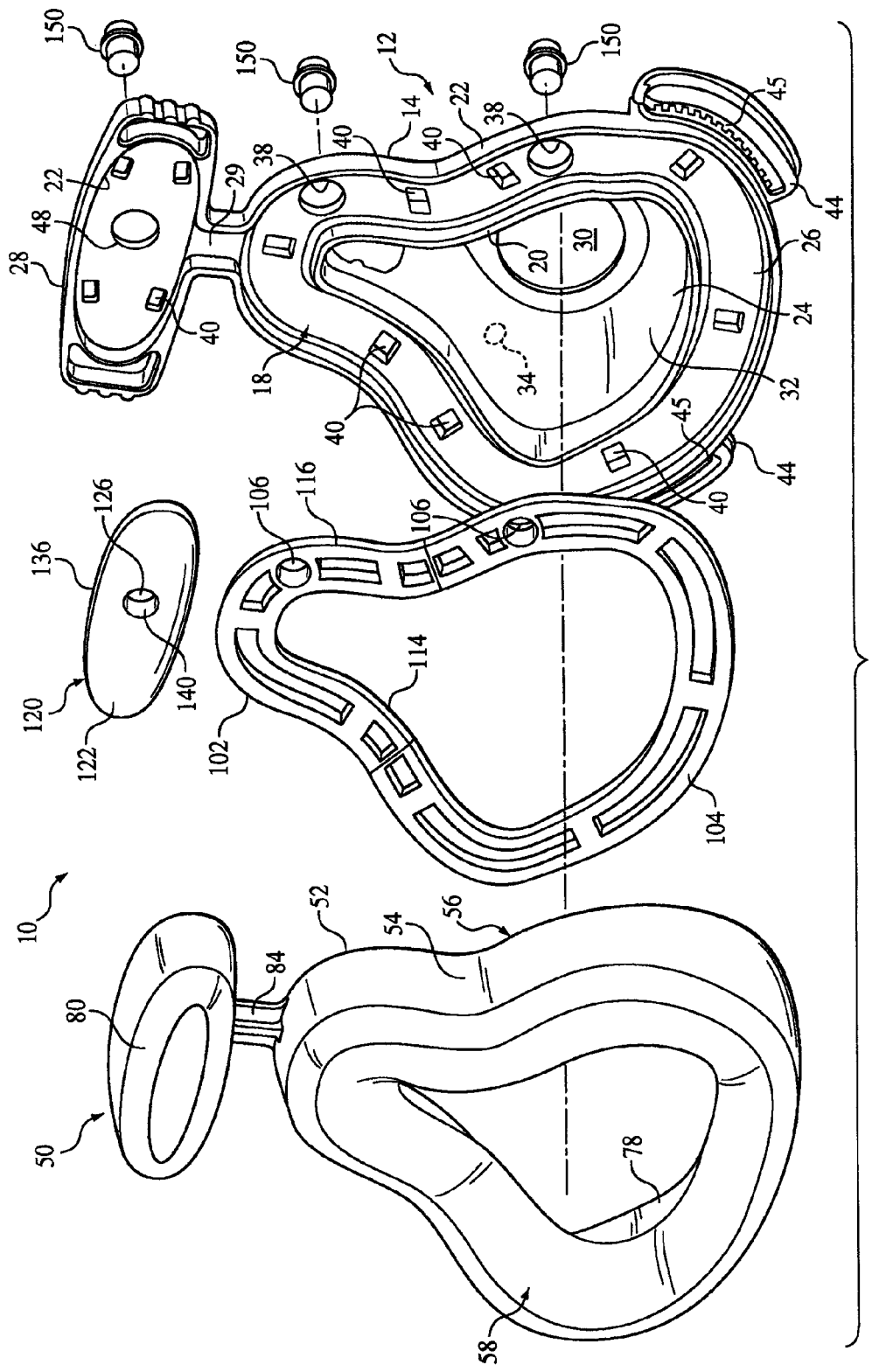
FIG. 5 is a second exploded perspective of the respiratory mask of FIG. 1.
Figure 6:
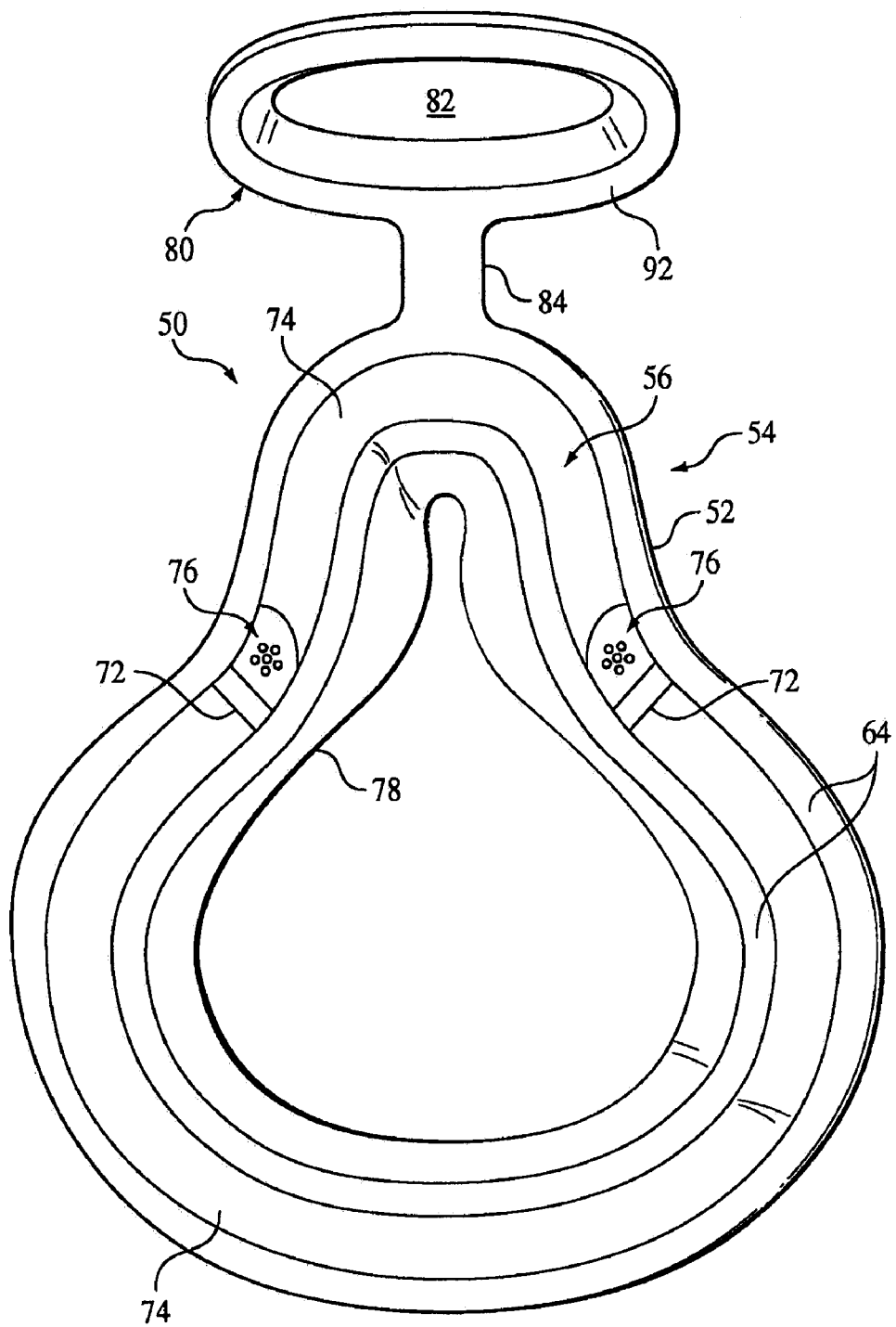
FIG. 6 is a rear view of a bladder forming an inflatable cushion of the respiratory mask of FIG. 1.
Figure 7:
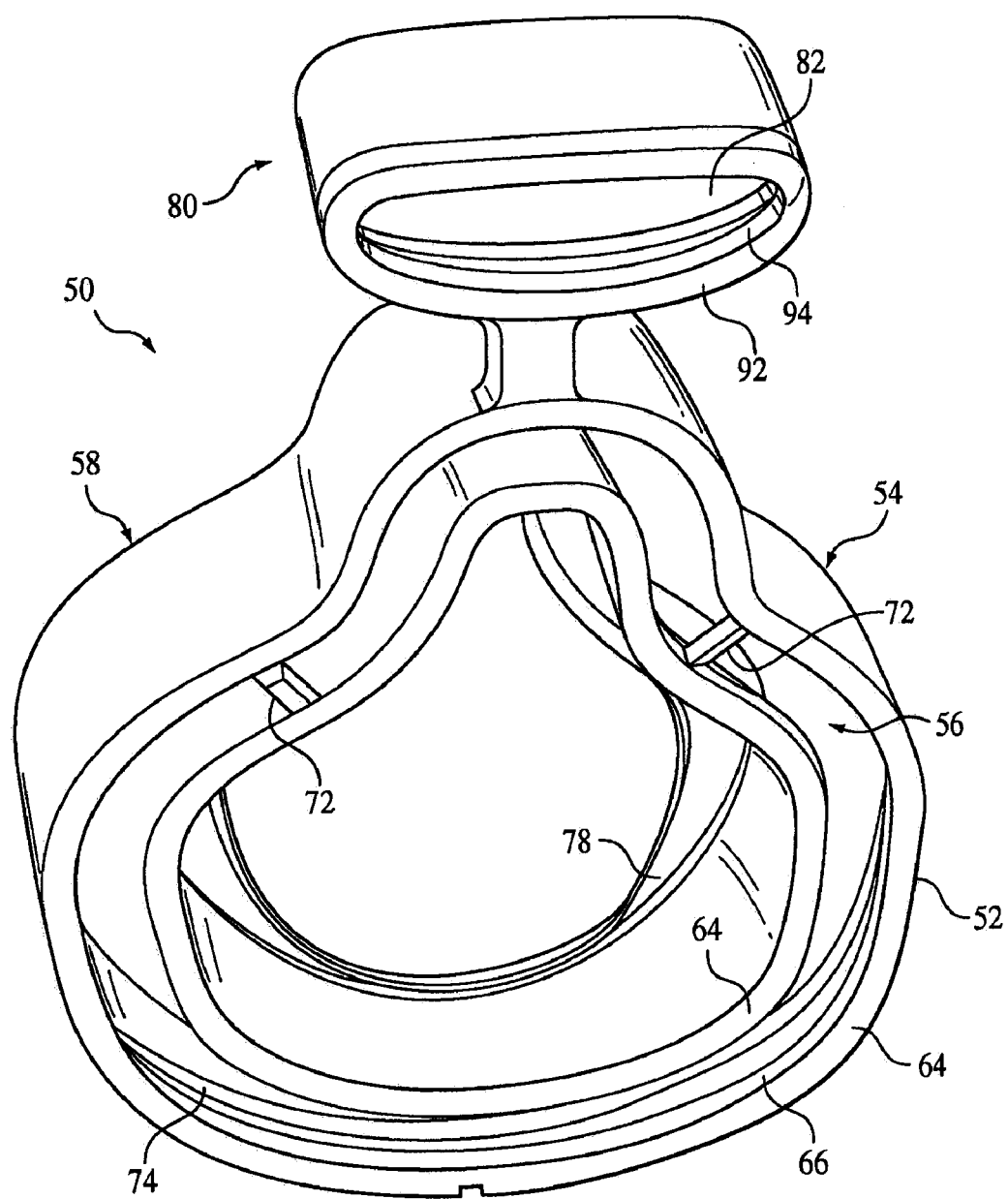
FIG. 7 is a perspective view of the bladder shown in FIG. 6.
Figure 8:
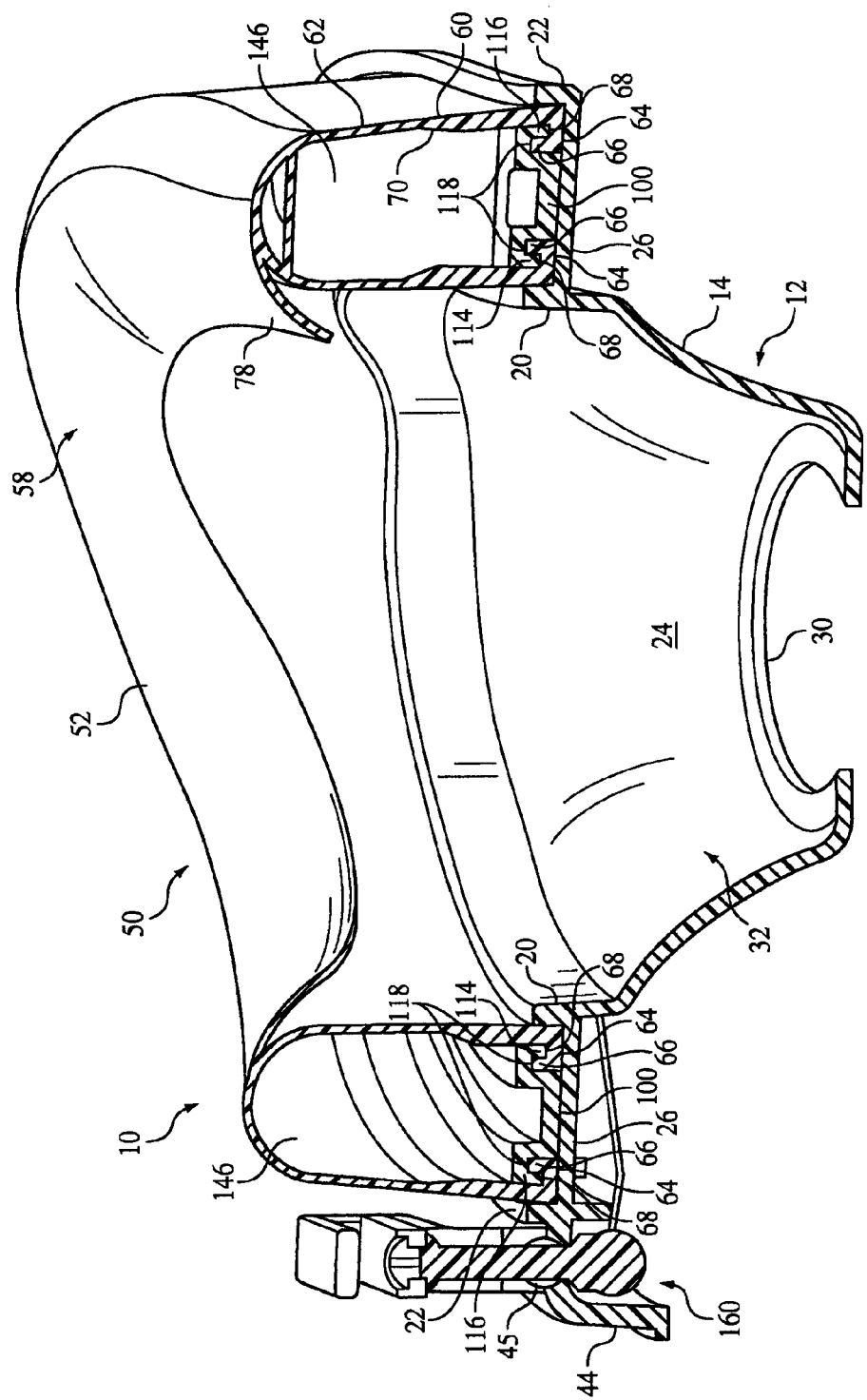
FIG. 8 is a generally transverse cross-sectional view of the respiratory mask of FIG. 1 taken along line 8-8 in FIG. 1.
Figure 9:
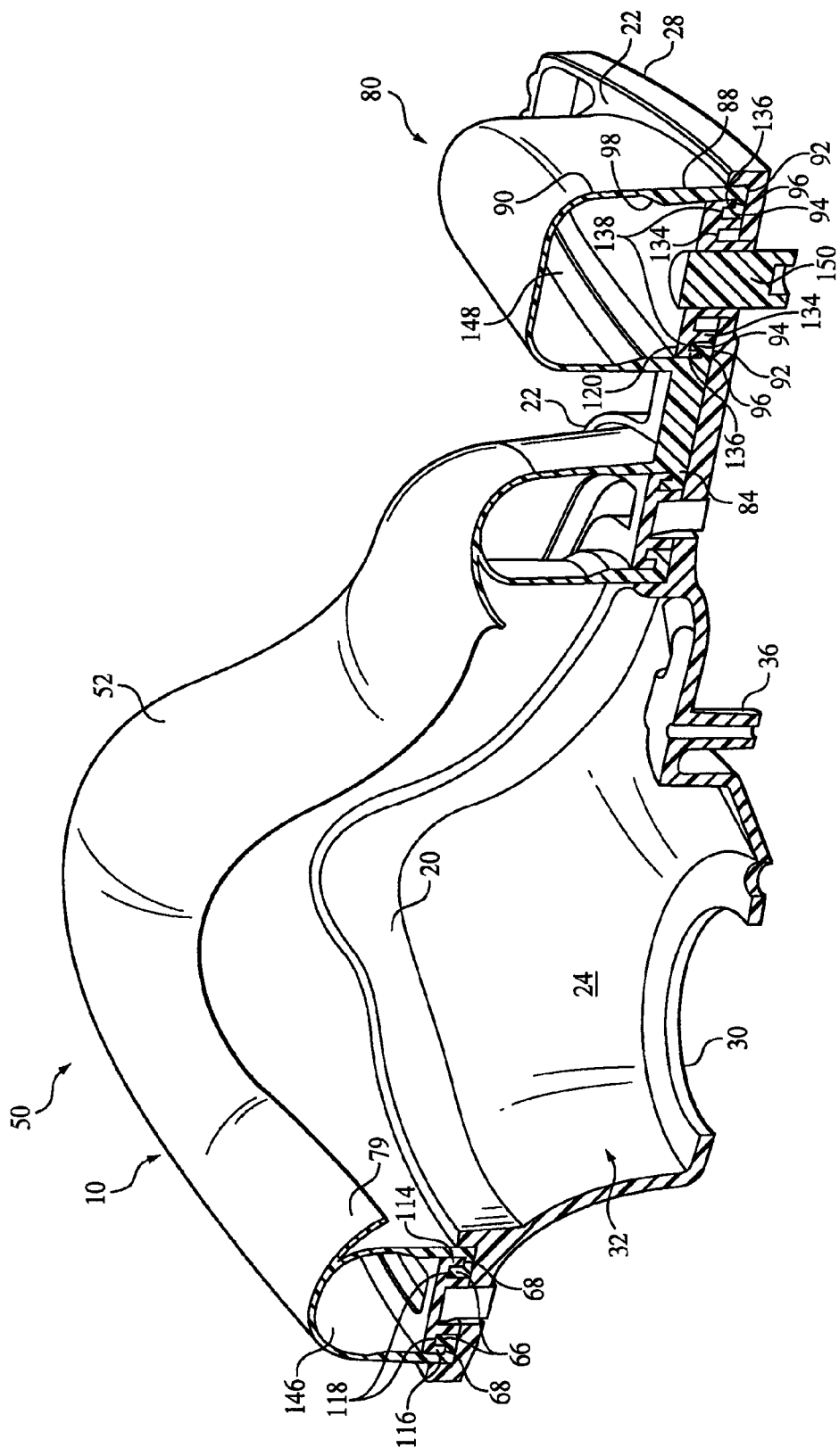
FIG. 9 is a generally longitudinal cross-sectional view of the respiratory mask of FIG. 1 taken along line 9-9 in FIG. 1.
Figure 10:
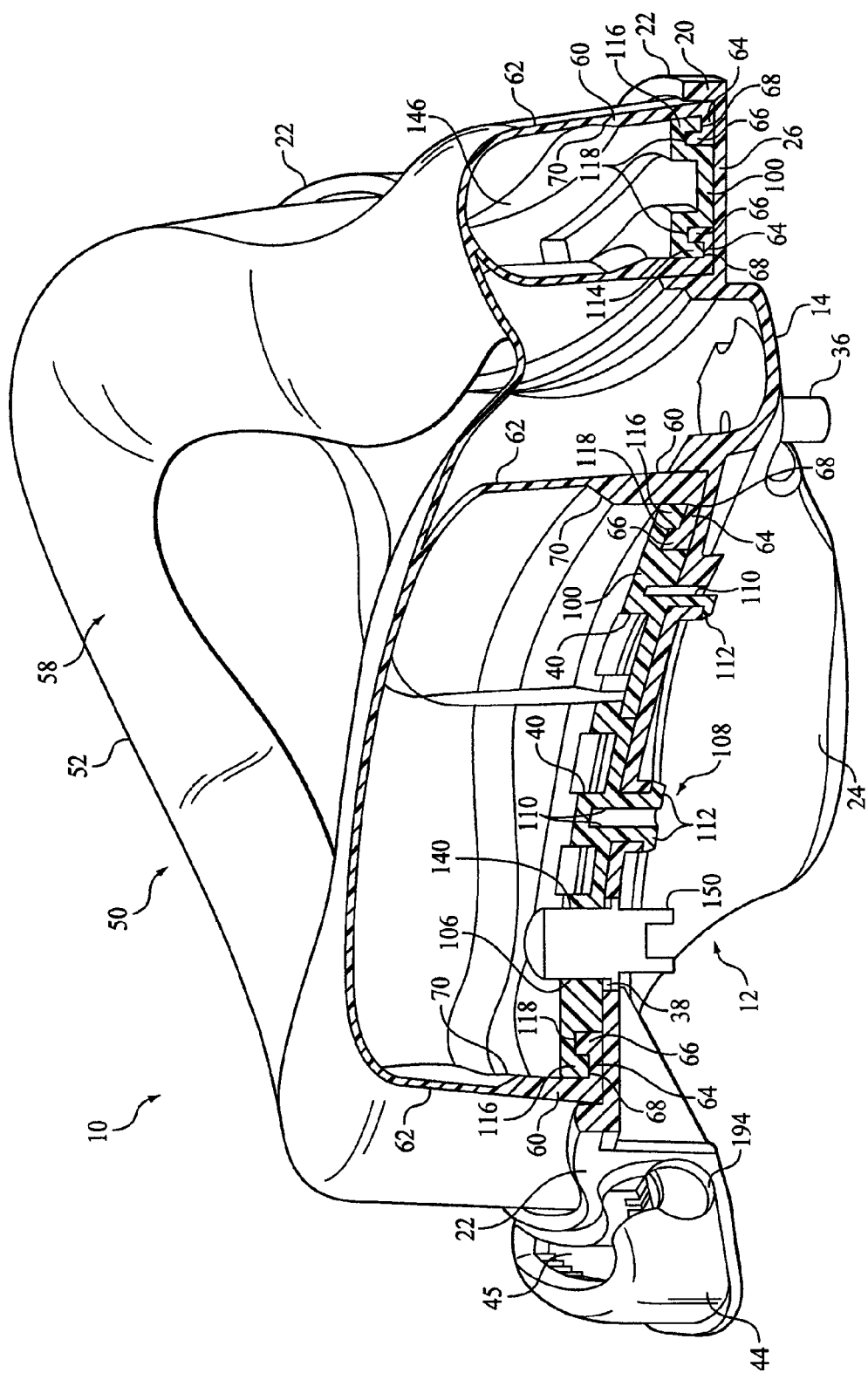
FIG. 10 is a second generally transverse cross-sectional view of the respiratory mask of FIG. 1 taken along line 10-10 in FIG. 1 and showing additional features.

As best illustrated in FIGS. 4 and 5 and as indicated previously, forehead retaining member 120 is typically provided as a separate attachment structure and is adapted specifically to attach forehead cushion 80 to forehead extension 28 extending from attachment flange 26 of base plate 14. Forehead retaining member 120 is generally adapted to engage forehead extension 28 and to provide a compressive force on inward-projecting or extending flanges 92 formed on forehead base portion 88 of forehead cushion 80 of bladder 52, so that a generally fluid tight seal is established between forehead cushion 80 and forehead extension 28. Forehead retaining member 120 generally comprises a plate-shaped body 122 which typically defines one inflation/deflation opening 126, generally positioned to coincide with the singular inflation opening 48 in forehead extension 28. Coinciding inflation openings 48, 126 generally support an inflation/deflation valve in substantially the same manner as the coinciding relationship between inflation openings 38 in attachment flange 26 and inflation openings 106 in first and second retaining members 102, 104 comprising retaining member 100. Inflation/deflation opening 126 will be referred to herein simply as inflation opening 126 for consistency.

As with retaining member 100 described previously, forehead retaining member 120 comprises a plurality of attachment tabs 128 extending from a bottom side thereof which are adapted to engage tab openings 40 in forehead extension 28 extending from attachment flange 26 of base plate 14 to secure forehead retaining member 120 to forehead extension 28. Attachment tabs 128 may come in any suitable form, but are depicted as being formed by a single prong 130 having a half arrow-shaped head 132, rather then the double prong configuration of attachment tabs 108 described previously. Prongs 130 of attachment tabs 128 operate in a generally analogous manner to prongs 110 of attachment tabs 108 described previously, and are adapted to flex as attachment tabs 128 are inserted into tab openings 40 in forehead extension 28 and then resiliently flex back substantially to their original orientation. As prongs 130 resilient flex back substantially to their original orientation, prong heads 132 overlap and engage raised lip or rim 43 projecting from the external side 16 of base plate 14 and, accordingly, the external side of forehead extension 28 to secure forehead retaining member 120 in engagement with forehead extension 28. The engagement of prong heads 132 of prongs 130 with raised rim 43 thereafter prevents removal of attachment tabs 128 from tab openings 40 in forehead extension 28.

Forehead retaining member 120 further comprises two closely spaced inner and outer lips or rims 134, 136, with outer lip 136 typically formed along an outer periphery of forehead retaining member 120. Attachment tabs 128 are typically formed to extend from inner lip 134, and inner lip 134 is formed to be slightly longer in length to project a greater distance outward from forehead retaining member 120 than outer lip 136. Typically, inner lip 134 is intended to contact the internal side of forehead extension 28 when forehead retaining member 120 is connected thereto. Peripheral outer lip 136 is intended to register with groove 96 defined by upstanding lip or rim 94 formed on inward-extending flange 92 formed on forehead base portion 88 of forehead cushion 80 of bladder 52. Inner lip 134 and peripheral outer lip 136 define a groove 138 therebetween for receiving the corresponding upstanding lip 94 formed on inward-extending flange 92 of forehead base portion 88 of forehead cushion 80 of bladder 52. The engagement of attachment tabs 128 with raised rim 43 on forehead extension 28 generally causes a compressive force to be exerted on inward-extending flange 92 to establish a generally fluid tight seal between forehead cushion 80 and forehead extension 28 as described further herein. Forehead retaining member 120 may be formed of a rigid plastic material such as polycarbonate, or any of the other materials disclosed previously in connection with base plate 14 and retaining member 100.

FIG. 4 shows several additional features present on retaining member 100 and forehead retaining member 120. Retaining member 100 and forehead retaining member 120 may each typically comprise a raised cylinder 140 extending around the periphery of inflation openings 106, 126 respectively. Cylinders 140 are typically raised sufficiently from retaining member 100 and forehead retaining member 120 to project or extend through corresponding inflation openings 38, 48 in attachment flange 26 and forehead extension 28, respectively. In particular, when retaining member 100 and forehead retaining member 120 are joined to attachment flange 26 and forehead extension 28, respectively, cylinders 140 pass or extend through inflation openings 38, 48 thereby facilitating assembly of respiratory mask 10. Retaining member 100 depicted in FIG. 4, as indicated previously, illustrates the possible segmentation of the retaining member 100 in separate pieces. First retaining member 102, which defines a generally U-shape in plan view, may comprise an overlap tab 142 at each end. Overlap tabs 142 are generally adapted to engage corresponding receiving recesses 144 formed in the ends of second retaining member 104 to form an overlapping engagement between first and second retaining members 102, 104. When first and second retaining members 102, 104 are overlapped as indicated, retaining member 100 is substantially continuous and corresponds generally to the internal shape of main body portion 54 of bladder 52.

With the constituent components of respiratory mask 10 substantially described, assembly of respiratory mask 10 will now be generally outlined with continued reference to FIGS. 1-10. The assembly of respiratory mask 10 is a multi-step process that begins with the attachment of bladder 52 to retaining member 100 and forehead retaining member 120. More particularly, main body portion 54 of bladder 52 is associated with retaining member 100 and forehead cushion 80 is associated with forehead retaining member 120. Thereafter, this component structure is secured to attachment flange 26 and forehead extension 28 on base plate 14, respectively. In the assembly process, retaining member 100 is inserted into the general U-shaped transverse cross section defined by main body portion 54 of bladder 52. Attachment tabs 108 projecting from the bottom side of retaining member 100 will face outward from main body portion 54. As retaining member 100 is inserted into main body portion 54, opposing flanges 64 formed on base portion 60 wrap around retaining member 100 and upstanding lips 66 on opposing flanges 64 engage grooves 118 defined by inner and outer peripheral lips 114, 116 on retaining member 100. Additionally, inner and outer peripheral lips 114, 116 on retaining member 100 correspondingly engage grooves 68 defined by upstanding lips 66 on opposing flanges 64, thereby forming overlapping and inter-engaging connections between retaining member 100 and main body portion 54 of bladder 52.

With main body portion 54 of bladder 52 now generally joined with retaining member 100, the one or more internal pockets 74 defined by internal dividers 72 in main body portion 54 of bladder 52 are enclosed by retaining member 100 thereby defining one or more enclosed internal chambers 146 in bladder 52. Internal chambers 146 are generally bounded or defined by main body portion 54 of bladder 52 and the side of retaining member 100 now enclosed by main body portion 54 of bladder 52. The number of internal chambers 146 is determined by the number of internal dividers 72 in main body portion 54 of bladder 52. Retaining member 100, as indicated, may comprise a multi-piece structure, and each component of retaining member 100, namely, first and second retaining members 102, 104, may be separately joined with main body portion 54 of bladder 102 according to the foregoing process.

A similar procedure to the foregoing is generally followed to join forehead retaining member 120 with forehead cushion 80. In particular, forehead retaining member 120 is inserted into forehead internal pocket 82 defined by forehead cushion 80 with attachment tabs 128 extending outward from internal pocket 82. Inward-extending flange 92 formed on forehead base portion 88 of forehead cushion 80 of bladder 52 wraps around the periphery of forehead retaining member 120, and upstanding rim 94 on inward-extending flange 92 engages outer groove 138 defined between inner lip 134 and peripheral outer lip 136 on forehead retaining member 120. As a result, peripheral outer lip 136 on forehead retaining member 120 will substantially engage groove 96 defined by upstanding rim 94 on inward-extending flange 92, thereby forming overlapping and inter-engaging connections between forehead retaining member 120 and forehead cushion 80. With forehead cushion 80 now joined with forehead retaining member 120, forehead internal pocket 82 is enclosed by forehead retaining member 120 to form and enclosed forehead internal chamber 148. Forehead internal chamber 148 is bounded by forehead cushion 80 and the side of forehead retaining member 120 disposed in forehead internal pocket 82.

With retaining member 100 joined to main body portion 54 of bladder 52 and forehead retaining member 120 joined to forehead cushion 80 of bladder 52, this combined structure may be secured to base plate 14. This component structure is typically attached to base plate 14 by inserting attachment tabs 108 into the corresponding tab openings 40 in attachment flange 26. As attachment tabs 108 are inserted into the corresponding tab openings 40, prongs 110 of attachment tabs 108 resiliently flex toward one another (e.g., inward). As the prong heads 112 on prongs 110 move toward one another, attachment tabs 108 are able to pass through the respective tab openings 40 in attachment flange 26. Once prong heads 112 pass through tab openings 40, prongs 110 are free to resiliently flex outward and prong heads 112 engage the respective raised rims 42 extending about tab openings 40, which prevents subsequent removal of attachment tabs 108 from tab openings 40.

A similar process is followed to secure forehead retaining member 120 and forehead cushion 80 to forehead extension 28 of base plate 14. Attachment tabs 128 on forehead retaining member 120 are inserted into the corresponding tab openings 40 in forehead extension 28. As attachment tabs 128 are inserted into corresponding tab openings 40 in forehead extension 28 singular prongs 130 resiliently flex to allow prong heads 132 to pass through tab openings 40. As prong heads 132 pass through tab openings 40, prongs 130 are free to resiliently return substantially to their original orientation. Prong heads 132 thereafter overlap and engage raised lip 43 on forehead extension 28 to secure forehead retaining member 120 in engagement with forehead extension 28. The engagement of prong heads 132 with raised oval lip 43 thereafter prevents removal of attachment tabs 128 from tab openings 40 in forehead extension 28.

As indicated previously, the insertion of attachment tabs 108 into corresponding tab openings 40 in attachment flange 26 and subsequent engagement with raised rims 42 around the respective tab openings 40 causes a compressive force to be exerted on opposing flanges 64 formed on base portion 60 of main body portion 54 of bladder 52. Opposing flanges 64, are sandwiched between retaining rim 100 and attachment flange 26. The applied compressive force causes opposing flanges 64 to deform and form a generally fluid tight seal between the opposing flanges 64 and attachment flange 26 of base plate 14. In particular, the applied compressive force causes upstanding rims 66 on opposing flanges 64 to deform and fill any open space in inner and outer grooves 118 in retaining member 100. Likewise, the applied compressive force causes inner and outer peripheral lips 114, 116 on retaining member 100 to fully engage inner and outer grooves 68 defined by upstanding rims 66 on opposing flanges 64 and press down into grooves 68. This overlapping, interlocking, and compressive engagement along with the deformable nature of the material comprising bladder 52 causes a generally fluid tight seal to be established between main body portion 54 of bladder 52 and attachment flange 26 of base plate 14.

A similar, generally fluid tight seal is established between forehead cushion 80 of bladder 52 and forehead extension 28 extending from attachment flange 26 on base plate 14. As indicated previously, the insertion of attachment tabs 128 into corresponding tab openings 40 in forehead extension 28 and subsequent engagement with raised lip 43 on the external side of forehead extension 28 causes a compressive force to be exerted on inward-extending flange 92 formed on forehead base portion 88 of forehead cushion 80 of bladder 52. Flange 92 is now sandwiched between forehead retaining member 120 and forehead extension 28. The applied compressive force causes inward-extending flange 92 to deform and form a generally fluid tight seal between inward-extending flange 92 and forehead extension 28. In particular, the applied compressive force causes upstanding lip 94 on inward-extending flange 92 to deform and fill any open space in groove 138 defined between defined between inner lip 134 and peripheral outer lip 136 on forehead retaining member 120. Likewise, the applied compressive force causes peripheral outer lip 136 on forehead retaining member 120 to fully engage groove 96 defined by upstanding lip 94 and press down upon flange 92. This overlapping, interlocking, and compressive engagement along with the deformable nature of the material comprising bladder 52 forms a generally fluid tight seal between the forehead cushion 80 of bladder 52 and forehead extension 28 extending from attachment flange 26 of base plate 14.

As indicated previously, base plate 14 includes inflation openings 38 and retaining member 100 includes inflation openings 106 positioned to coincide with inflation openings 38. Likewise, forehead extension 28 includes an inflation opening 48 and forehead retaining member 120 includes an inflation opening 126 positioned to coincide with inflation opening 48. The raised cylinders 140 associated with inflation openings 106, 126 project or extend through corresponding inflation openings 38, 48 in attachment flange 26 and forehead extension 28 when retaining member 100 and forehead retaining member 120 are joined to base plate 14. Once retaining member 100 and forehead retaining member 120 are secured to base plate 14, inflation valves 150 may be inserted into respective inflation openings 38, 48 in base plate 14. Inflation valves 150 extend through inflation openings 38, 48 to engage inflation openings 106, 126 in retaining member 100 and forehead retaining member 120, respectively. Inflation valves 150 may be secured in now continuous openings defined by inflation openings 38, 106 and 48, 126 by a friction fit connection or by other suitable means such as by a medical grade adhesive.

Inflation valves 150, in the present embodiment of respiratory mask 10 illustrated in FIGS. 1-10, are typically bi-directional valves, adapted to allow a fluidizing medium to be introduced into internal chambers 146, 148 of respiratory mask 10, and then released or removed therefrom. While air is envisioned as the most readily obtainable fluidizing medium, this disclosure is not intended to be limited to this medium. Other gases may be used as the fluidizing medium. Additionally, the fluidizing medium may be a liquid such as mineral oil or saline solutions as examples, a solid such as a gel, or any combination of a gas, liquid, or solid medium. Moreover, the fluidizing medium is further envisioned as possibly being provided in solid form, such as a powdery solid. An example of a suitable inflation/deflation or bi-directional valve for inflation valves 150 suitable for handling a gaseous fluidizing medium, such as air, is manufactured by Respironics, Inc., the assignee of the present application, and disclosed in U.S. Pat. No. 4,913,401 to Handke incorporated herein by reference in its entirety. Inflation valves 150 allow for the fluidizing medium to pass into and removed from internal chambers 146, 148 through the same opening or aperture. Inflation valves 150 will allow the respective internal chambers 146, 148 to be pressurized to different inflation pressures when a gaseous fluidizing medium is used, thereby allowing respiratory mask 10 to be customized to suit the individual wearer.

Figure 11:
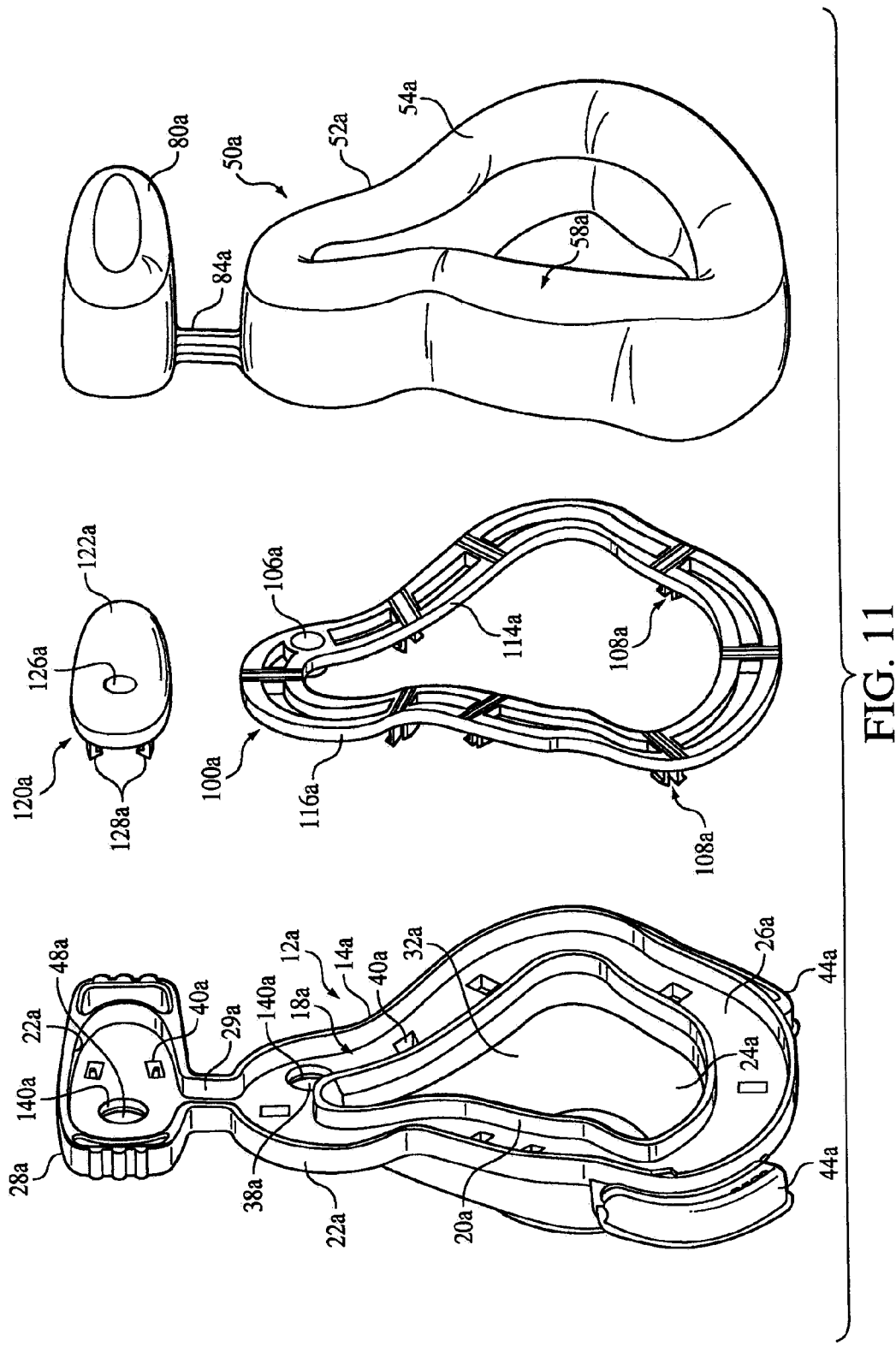
FIG. 11 is an exploded perspective view of another embodiment of the respiratory mask of FIG. 1.
Figure 12:
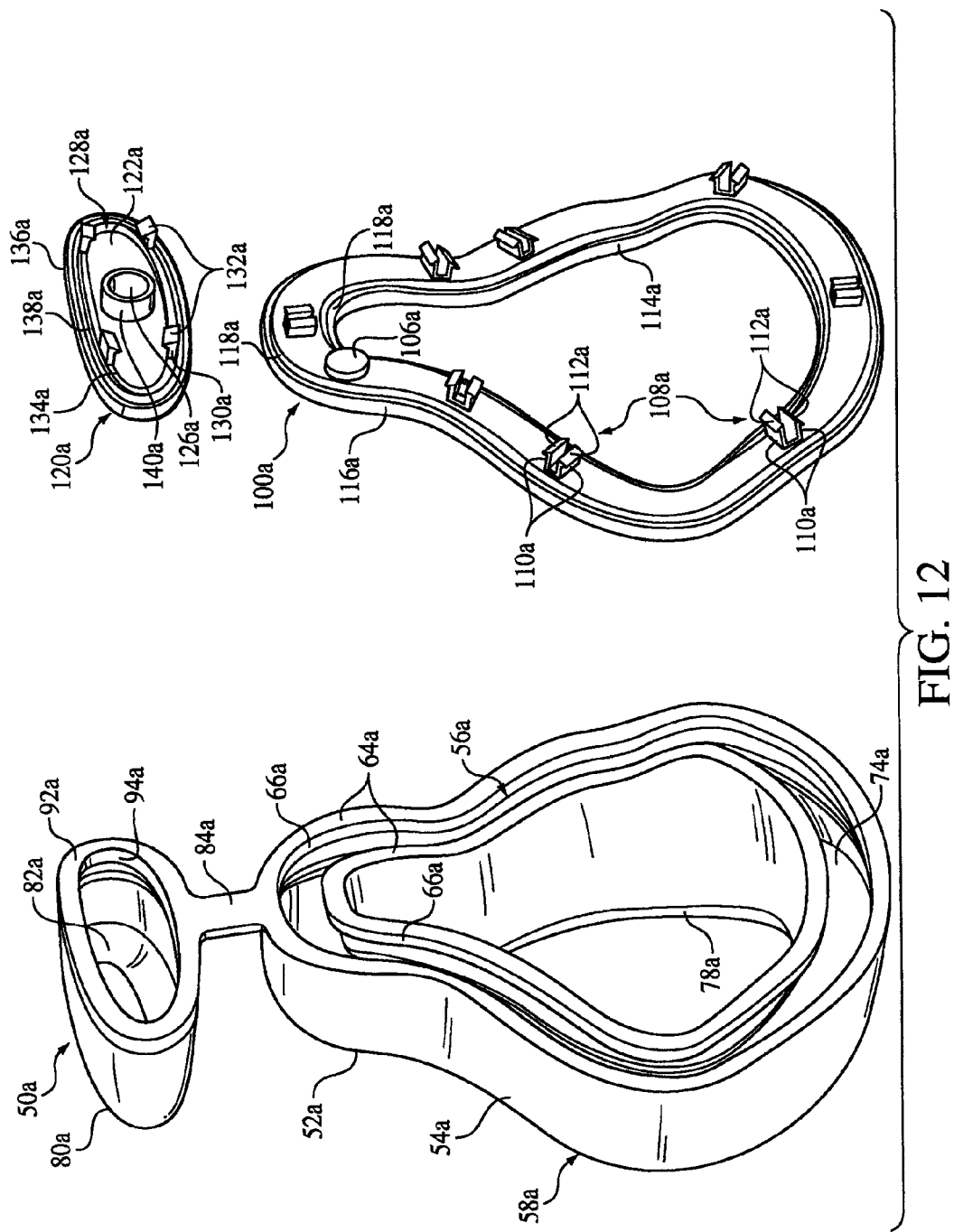
FIG. 12 is an exploded perspective view of the respiratory mask of FIG. 11 showing only a bladder and retaining member of the mask.

Another embodiment of respiratory mask is shown in FIGS. 11 and 12 wherein like elements have been given the same reference numbers annotated by the letter "a." This embodiment is substantially identical to respiratory mask 10 described hereinabove but comprises a unitary retaining member 100a or retaining "ring" 100a. The primary difference between respiratory mask 10a and respiratory mask 10 relates to the structure of main body portion 54a of bladder 52a. Main body portion 54a of bladder 52a is now formed without internal dividers 72. As a result, bladder 52a and, more particularly, main body portion 54a of bladder 52a defines a single, continuous, and circumferentially-extending internal pocket 74a. Since a single internal pocket 74a is present in main body portion 54a of bladder 52a, retaining member 100a no longer needs to be segmented to conform to the number of internal chambers 74a in bladder 52a and may be provided as a unitary ring structure or member. Additionally, retaining member 100a may also be formed with a single inflation opening 106a which may coincide with a single inflation opening 38a in attachment flange 26a of base plate 14a. However, multiple corresponding or coinciding inflation openings 38a, 106a may still be provided. Other than the foregoing, respiratory mask 10a is substantially identical to respiratory mask 10 described hereinabove, and the foregoing structural and assembly descriptions relating to respiratory mask 10 are generally applicable to respiratory mask 10a. It will be clear to those skilled in that art that only a single inflation valve 150a is required for respiratory mask 10a.

Figure 14A:
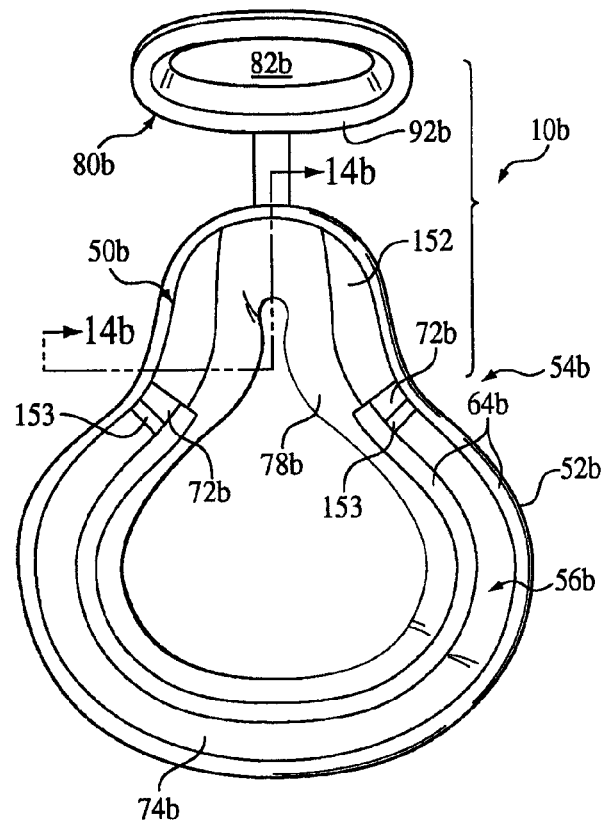
FIG. 14a is a rear view of an inflatable rim with an attached forehead cushion used in a further embodiment of the respiratory mask.
Figure 14B:
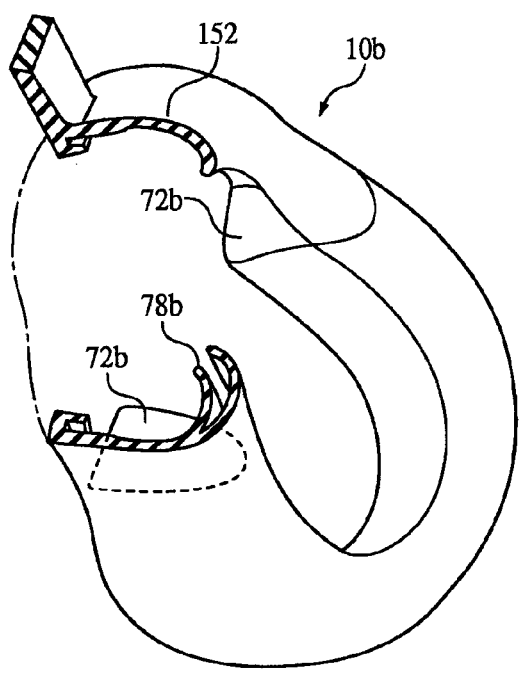
Figure 15:
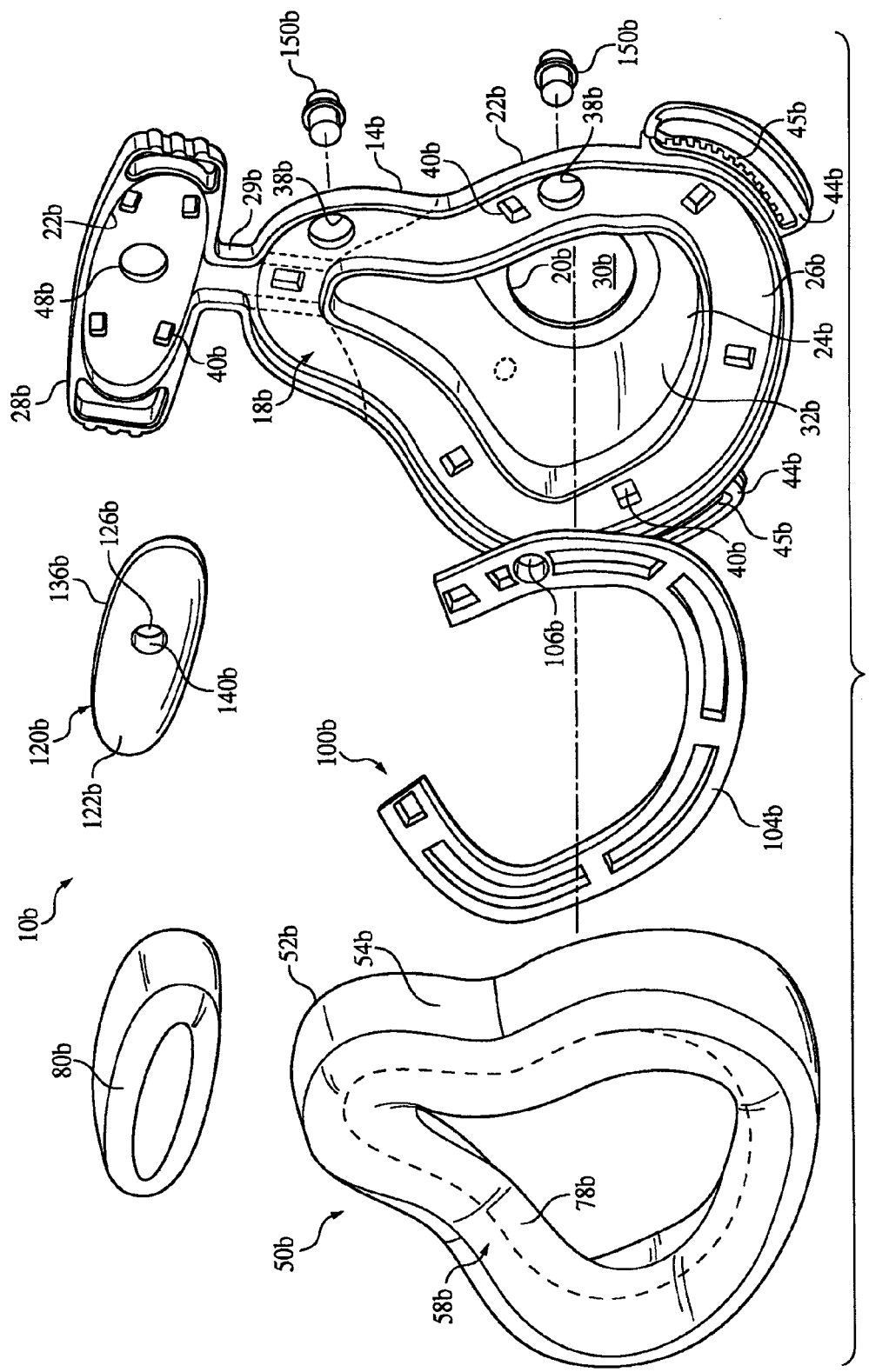
FIG. 15 is an exploded perspective showing an embodiment of the respiratory mask of FIG. 1.

Referring to FIGS. 14a-15, another embodiment is shown wherein like elements have been given the same reference numbers annotated with the letter "b." The respiratory mask 10b, main body portion 54b of bladder 52b is formed without an "upper" internal pocket 74b extending between internal dividers 72b. In this embodiment, a simple flap member or membrane structure 152 is formed as part of bladder 52b and extends between internal dividers 72b. Flap member 152 takes the place of the upper internal pocket 74b defined by bladder 52b, and the U-shaped cross-section of bladder 52b forming upper-internal pocket 74b. Flap member 152 will thus extend between internal dividers 72b to form a thin flap of material that will generally encompass a wearer's nose, while the "lower" internal pocket 74b in main body portion 54b begins generally at internal dividers 72b and forms a continuous internal pocket 74b that extends around the wearer's mouth when respiratory mask 10b is in place on the wearer's face. Flap member 152 may also include a sealing flap 78b as shown in FIGS. 14a and 14b.

When respiratory mask 10a is in place on a wearer's face, internal dividers 72b are typically positioned substantially on or slightly below the wearer's cheekbones so that flap member 152 may extend from the internal dividers 72b, along the sides of the wearer's nose and cover the bridge of the wearer's nose. As represented by dashed lines in FIG. 15, portions of base plate 14b may be removed in the area generally corresponding to "missing" upper internal pocket 74b. Respiratory mask 10b will thereby have a smaller profile lengthwise profile. As also shown in dashed lines, forehead extension 28b may extend directly from internal rim 20b on attachment flange 26b. Forehead extension 28b will typically support forehead cushion 80b. The forehead cushion may be joined together with the main body 54b as shown in FIG. 14a. Alternatively, the forehead cushion 80b may be separate from the main body 54b as shown in FIG. 15.

In summary, flap member 152 is typically a thin membrane of material that forms about the top one-third of main body portion 54b of bladder 52b and is specifically sized and adapted to substantially cover the nose of the wearer of respiratory mask 10b. The bottom approximately two-thirds of main body portion 54b of bladder 52b is formed in the manner described previously in this disclosure, and may be secured to base plate 14b and attachment flange 26b in particular by retaining member 100b in the manner described previously. Retaining member 100b may omit the "top" or first retaining member 102b (not shown) and comprise only the "bottom" or second retaining member 104b for securing main body portion 54b of bladder 52b to attachment flange 26. The inner periphery of flap member 152 is typically secured directly to inner rim 20b on attachment flange 26b or to covering portion 24 of base plate 14b to form a fluid tight seal with base plate 14. Sealing flap 78b may be formed to extend from the outer periphery of flap member 152 which contacts the wearer. If desired, sealing flap 78b may be omitted from flap member 152. Furthermore, internal dividers 72b may be formed with registering structure 153 adapted to engage receiving recess 144b at the ends of second retaining member 104b to ensure a generally fluid tight seal is established between bladder 52b and attachment flange 26b in the vicinity of internal dividers 72b when the second retaining member 104b is used to secure bladder 52b to attachment flange 26b of base plate 14b.

Referring to FIGS. 16-20, respiratory masks 10, 10a, 10b are each secured on a wearer's face by securing straps (not shown). As indicated previously, such straps are attached to latches 160 which secure the straps to respiratory masks 10, 10a, 10b. The straps are used to secure respiratory masks 10, 10a, 10b to a wearer's face. Typically, the straps extend around the wearer's head and are joined, for example, by a hook-and-loop connection. Alternatively, a single elastic strap having its ends secured base plate 14 via latches 160 may be used to secure respiratory masks 10, 10a, 10b to a wearer's face.

A variety of latches may be used to secure the straps to the masks such as a cam-style latch as described in International Patent Publication No. WO 00/78383, a ball-and-socket style latch as described in co-pending U.S. patent application Ser. No. 10/629,366 (assigned to the assignee of the present invention and hereby incorporated by reference), or the novel latch 160 described herein.

The details of latches 160 are described hereinafter in connection with respiratory mask 10 for convenience, but are equally applicable to respiratory masks 10a, 10b which exhibit only slight modifications to respiratory mask 10. Moreover, one of ordinary skill in the art can best appreciate that the unique latches as disclosed herein may be used in a variety of patient interfaces with, or without, a bladder. For instance, the latches may be used on respiratory masks as well as nasal cannulas without departing from the spirit or scope of the present invention.

Figure 16:
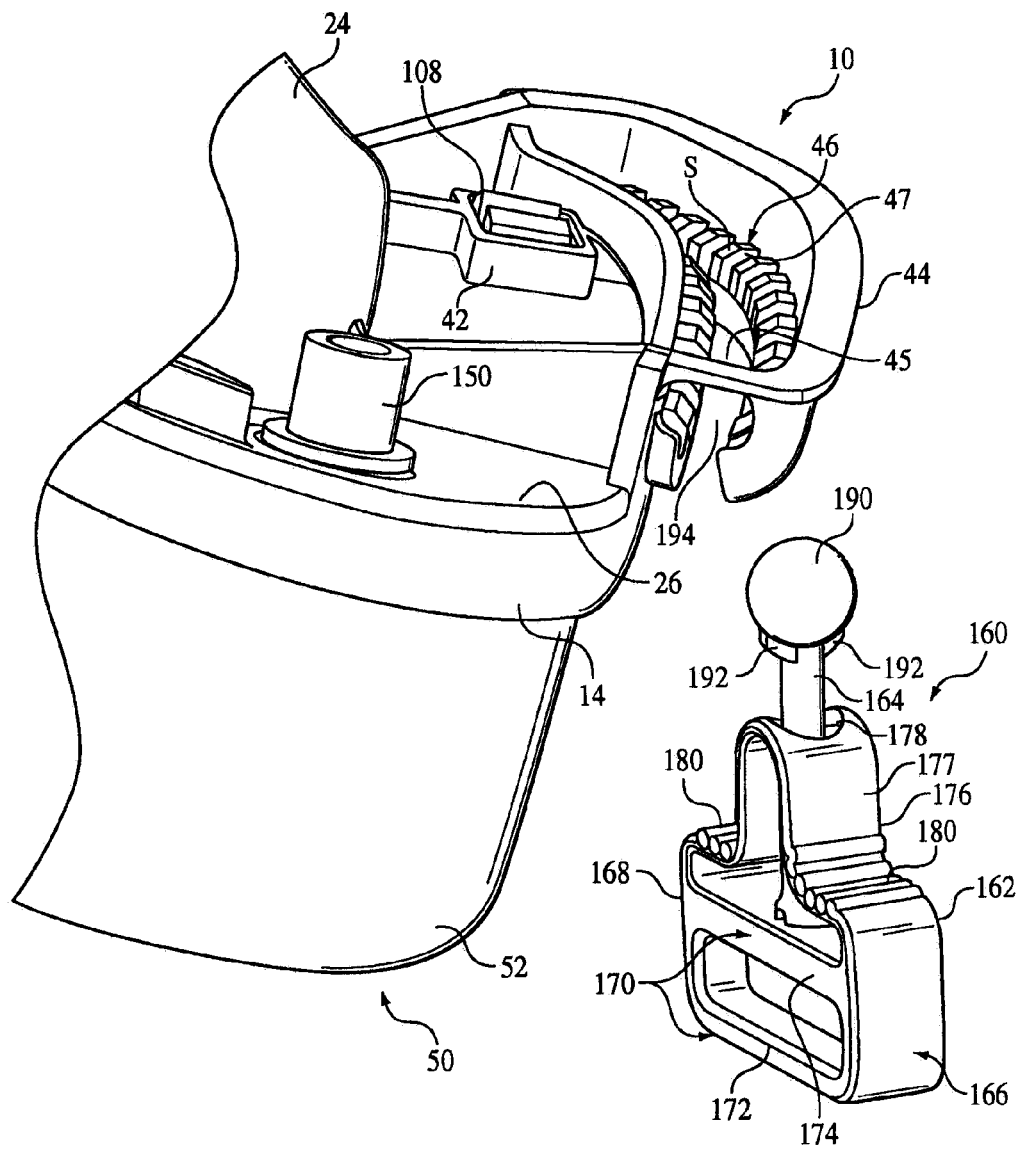
FIG. 16 is a perspective view of a portion of the respiratory mask of FIG. 1 showing a latch used to secure attachment straps to the mask.
Figure 17:
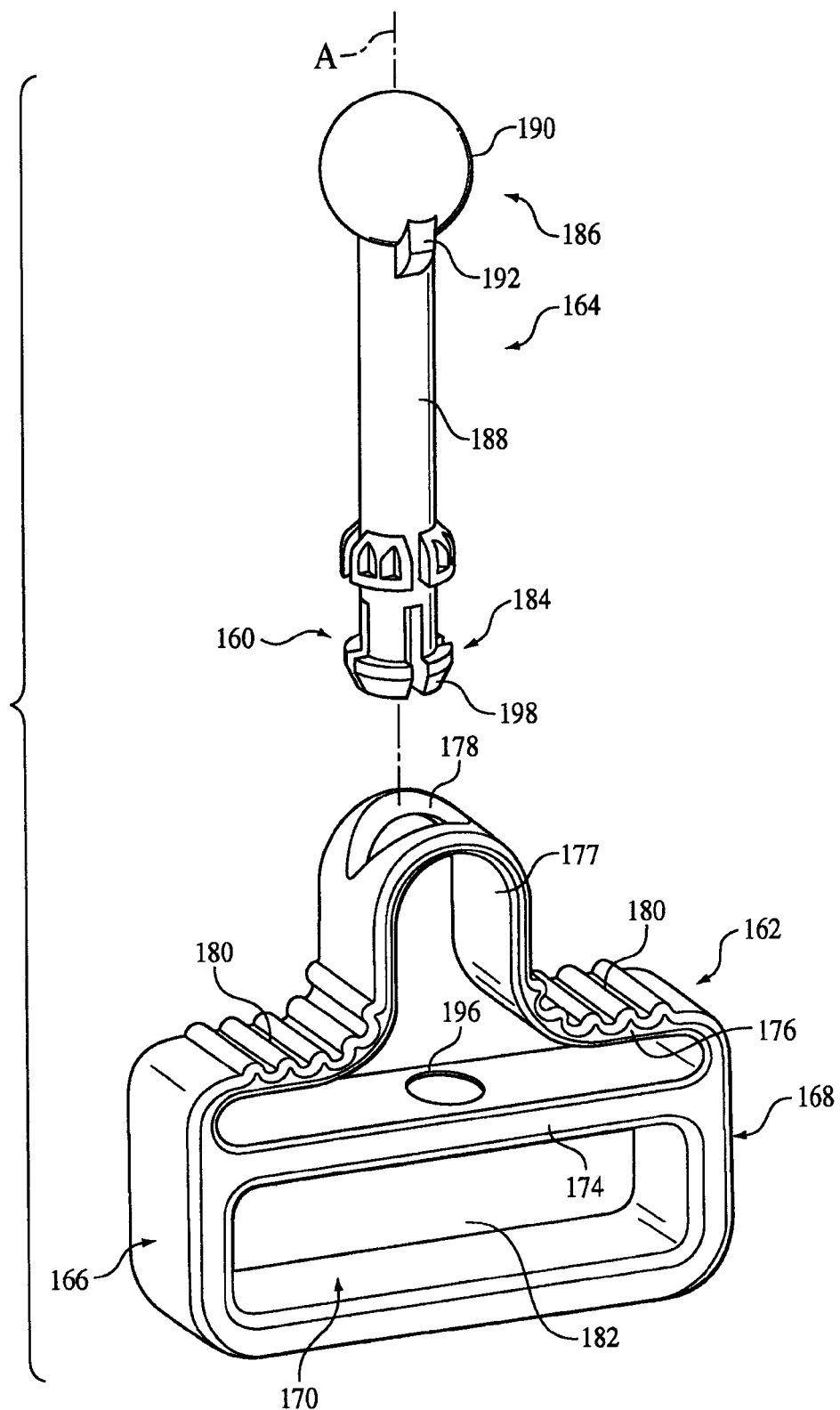
FIG. 17 is an exploded perspective view of the latch of FIG. 16 with the latch shown detached from the respiratory mask.
Figure 18:
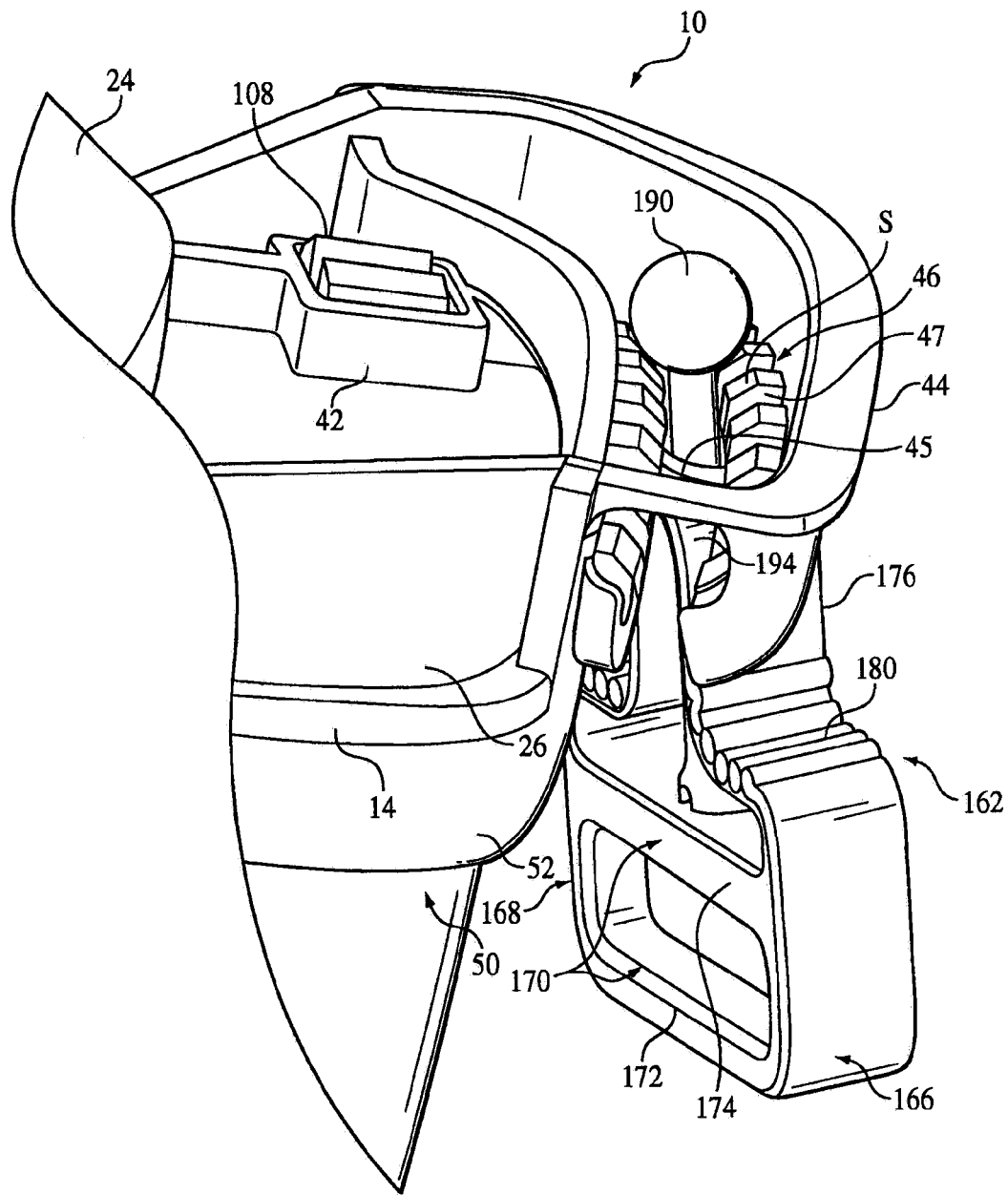
FIG. 18 is a perspective view showing the portion of the respiratory mask depicted in FIG. 16 with the latch associated with the respiratory mask.

A first embodiment of latches 160 is shown in FIGS. 16-18. As described previously, latches 160 are adapted to engage tracks 44 formed as part of attachment flange 26 on the external side 16 of base plate 14. Tracks 44 are generally arcuate shaped structures that are formed integrally with base plate 14 and are used to support latches 160. Tracks 44 comprise an arcuate or curved adjustment slot 45 having a plurality of engagement slots 46 disposed on opposite sides thereof for receiving projecting structure on latches 160 for securing latches 160 in a fixed, but releasable, position in tracks 44. Tracks 44 are disposed generally along the lower lateral sides of base plate 14 so that the straps associated with latches 160 may extend around a wearer's head along the wearer's left and right lower cheek areas. Engagement slots 46 are defined between a plurality of contact elements 47 disposed in tracks 44 on opposite sides of elongated, arcuate adjustment slot 45.

Each latch 160 is identical and is typically provided as a two-piece component, comprising a latch body 162 and a post member 164 engaged with latch body 162. Latch body 162 is typically a unitary structure having opposite sides or sidewalls 166, 168 typically connected by a plurality of connecting members 170. Connecting members 170 typically comprise a first connecting member 172 and a spaced apart second connecting member 174 each extending between opposite side 166, 168. A third connecting member 176 also connects opposite sides 166, 168 and comprises a U-shaped distal portion 177 that defines a central opening 178 through which post member 164 extends. Third connecting member 176 is typically deformable along a Central Axis A passing though post member 164, as described herein. Additionally, third connecting member 176 may be formed with finger grips 180 on opposite sides of distal portion 177 and central opening 178 for grasping by a person placing respiratory mask 10 on his or her own face or another person's face. Finger grips 180 are positioned to allow the user of respiratory mask 10 depress third connecting member 176 toward second connecting member 174 thereby extending post member 164 through central opening 178. First and second connecting members 172, 174 are spaced apart to define a strap-receiving opening 182 therebetween. An end of an attachment strap may be passed through strap-receiving opening 182 and then secured in strap opening 182, for example, by looping the end back against the attachment strap and securing it to the strap.

Post member 164 has a first or attachment end 184 adapted to engage second connecting member 174 and a second end 186. First and second ends 184, 186 are connected by a shaft 188. Second end 186 is formed with a spherical or ball detent 190 comprising depending engagement tabs 192 adapted to engage engagement slots 46 in tracks 44. As indicated previously, tracks 44 are each formed with an elongated, arcuate adjustment slot 45 having engagement slots 46 provided on opposite sides thereof. As shown in FIG. 16, a circular access opening 194 is provided in one end of each track 44 for receiving ball detent 190 therethrough. Engagement tabs 192 are provided on opposite lower sides of ball detent 190 for registering with engagement slots 46 in a releasable manner as described herein. First end 184 of post member 164 is secured in a receiving opening 196 defined in second connecting member 174, for example, by resiliently deflectable tabs 198 formed on first end 184. The engagement of deflectable tabs 198 in receiving opening 196 typically permits latch body 162 to pivot with respect to post member 164 to allow for adjustments of the orientation of the securing straps associated with strap opening 182 defined between first and second connecting members 172, 174.

Latch 160 is associated with track 44 by the user of respiratory mask 10 by applying downward pressure on finger grips 180. This downward pressure causes the third connecting member 176 to depress toward second connecting member 174 and causing post member 164 to project further from central opening 178 in distal portion 168 of third connecting member 176. This extending movement between increases the length of post member shaft 188 exposed from central opening 178. Ball detent 190 on post member 164 may then be inserted into ball shaped opening 194 defined at one end of track 44. Typically, ball detent 190 is oriented with engagement tabs 192 generally in line with adjustment slot 45 to allow ball detent 190 and engagement tabs 192 to pass through ball shaped opening 194. Once inserted into adjustment slot 45, additional clearance may be provided to allow post member 164 to be rotated to a position to allow engagements tabs 192 on ball detent 190 to engage two opposed engagement slots 46 in adjustment slot 45. To provide such clearance, the user of respiratory mask 10 may apply additional downward pressure to finger grips 180 thereby further extending post member 164 outward from central opening 178 in third connecting member 176 and positioning engagement tabs 192 above the selected opposed engagement slots 46. Latch body 162 may then be rotated which causes post member 164 to rotate in adjustment slot 45. As post member 164 is rotated, ball detent 190 and engagement tabs 192 are rotated until engagement tabs 192 are aligned with the selected engagement slots 46. The user may then release pressure on finger grips 180 which allows third connecting member 176 to resiliently return substantially to its initial orientation. When this occurs, distal portion 177 on third connecting member 176 will contact the outside surface of track 44 and post member 164 will withdraw axially in central opening 178 in third connecting member 176. This retracting movement causes engagement tabs 192 on ball detent 190 to engage engagement slots 46 in track 44 securing latch body 162 in a specific position in track 44.

Distal portion 177 of third connecting member 176 operates in an analogous manner to a leaf spring, which is deflected to allow adjustment of the position of latch 160 in track 44 and, upon release, secures the position of latch 160 in track 44. Moreover, distal portion 177 of third connecting member 176 will remain in contact with and apply a force against the outside surface of track 44 and prevent engagement tabs 192 from disengaging from engagement slots 46 until the user again applies downward force to finger grips 180. When it is desired to move latch 160 to a different position in track 44, the user again applies downward pressure on finger grips 180 which again causes post member 164 to project outward from central opening 178 and causes ball detent 190 to lift from contact from curved contact surface S on contact elements 47 and engagement tabs 192 to disengage from engagement slots 46, allowing post member 164 to moved to a different position in adjustment slot 45 by manipulating latch body 162. Once this pressure is released with post member 164 disposed at the desired location in track 44, engagement tabs 192 will engage a new pair of engagement slots 46 and ball detent 190 will engage contact elements 47 in the vicinity of the new engaged engagement slots 46. The distal portion 177 of third connecting member 176 will again contact the outside surface of track 44 and apply a force against track 44 to prevent the disengagement of ball detent 190 from contact elements 47 and, more particularly, disengagement of engagement tabs 192 from engagement slots 46.

Figure 19:
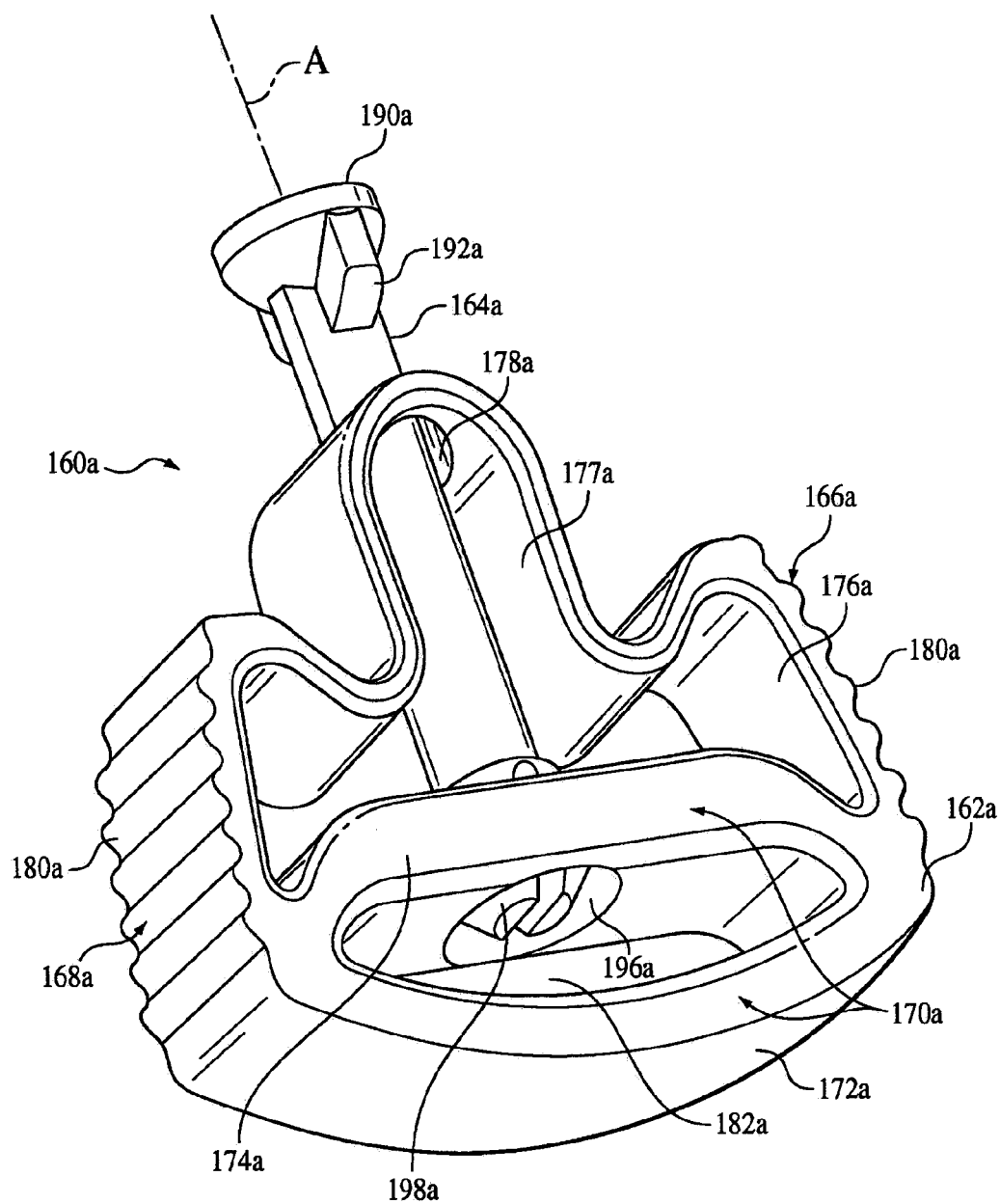
FIG. 19 is a perspective view of the latch according to another embodiment.
Figure 20:
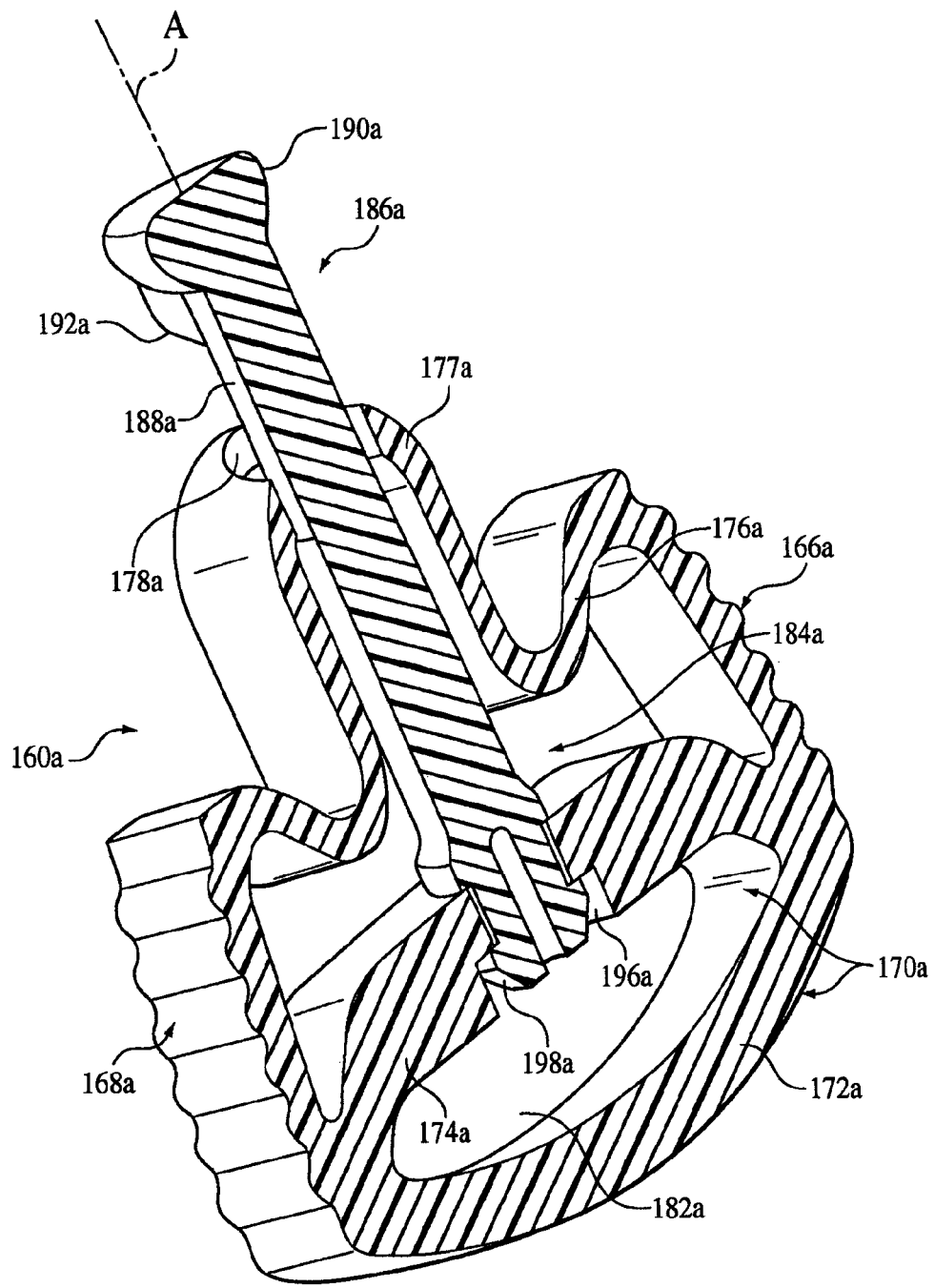
FIG. 20 is a longitudinal cross-sectional view of the latch of FIG. 19.
Figure 22:
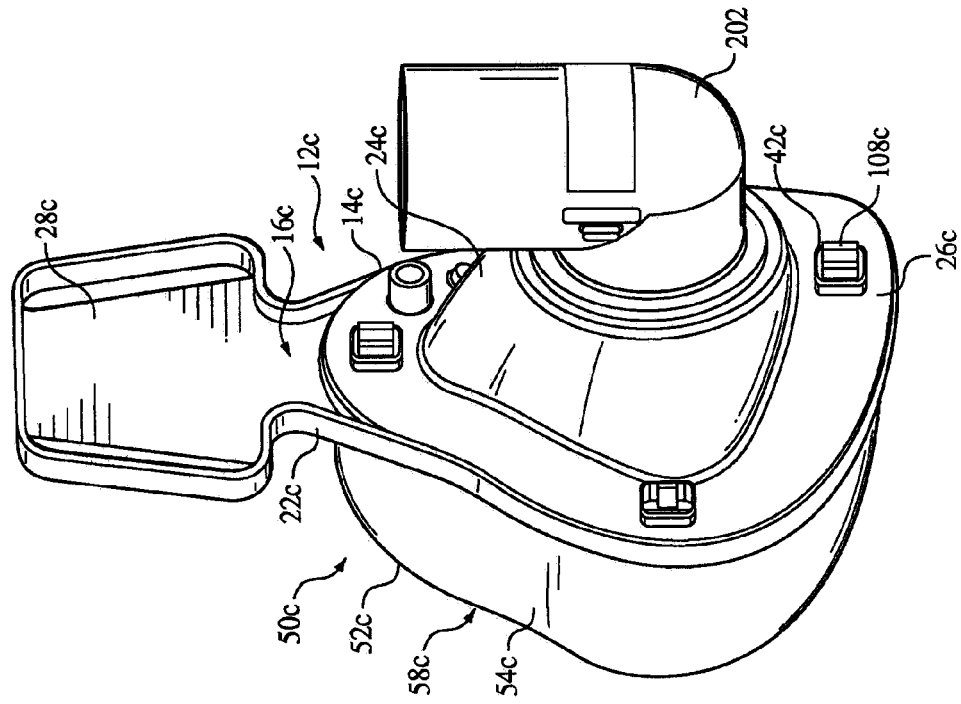
FIG. 22 is a perspective view of the respiratory mask of FIG. 21 viewed from a wearer-contacting side of the mask.
Figure 21:
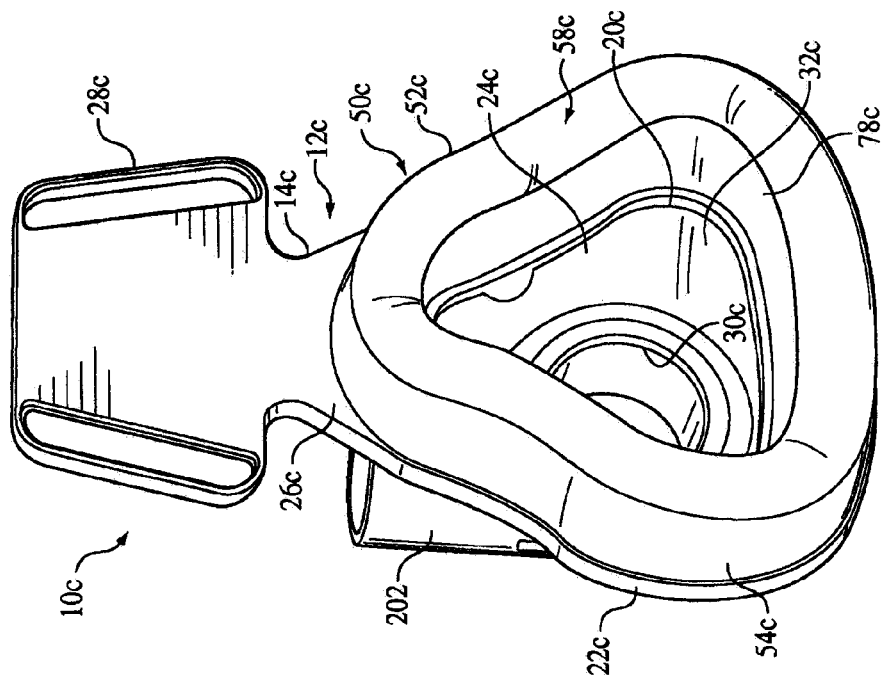
FIG. 21 is a perspective view of a nasal covering embodiment of the respiratory mask.
Figure 23:
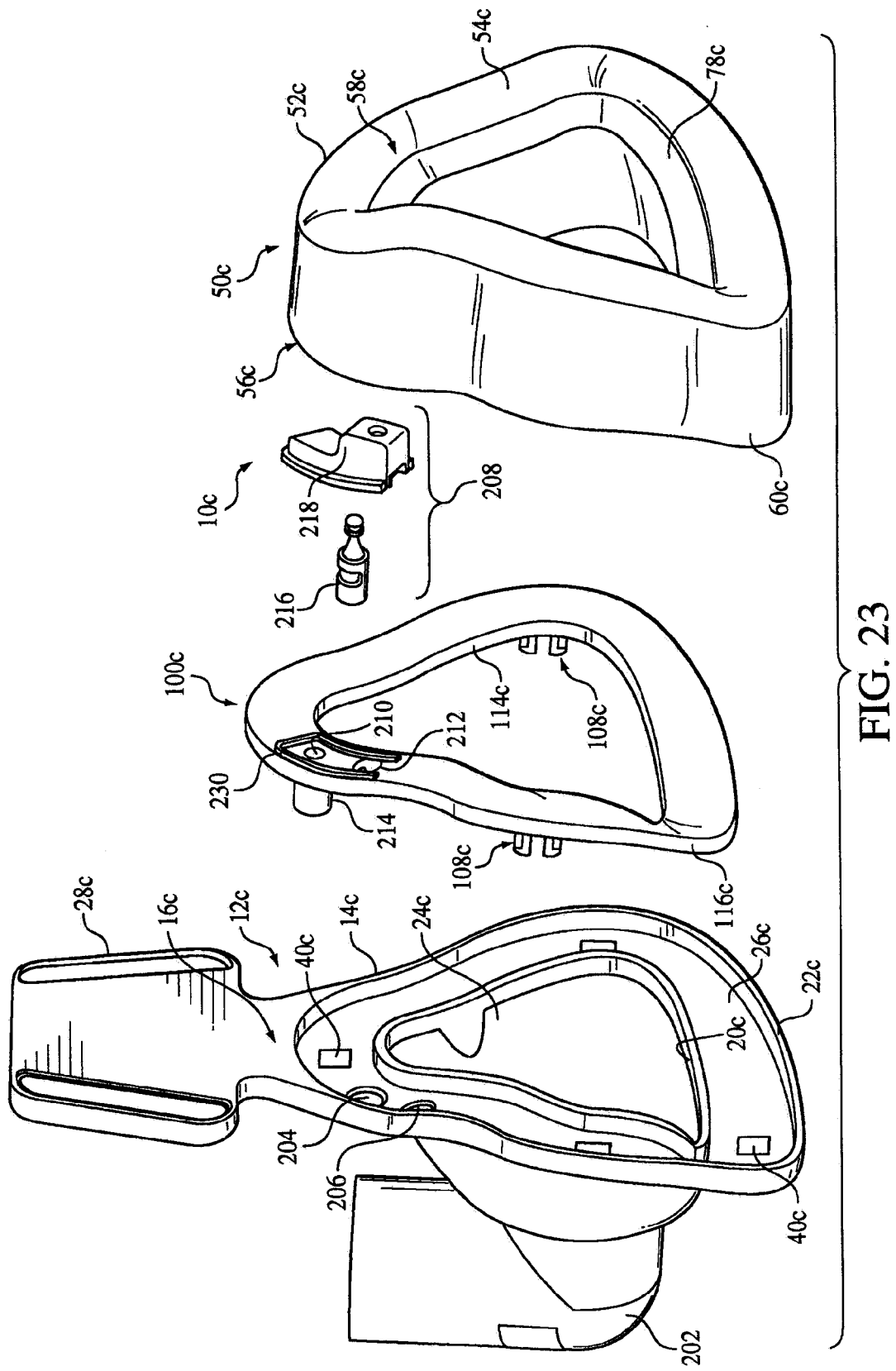
FIG. 23 is a perspective view of the respiratory mask of FIG. 21 viewed generally from the side of the mask.
Figure 24:
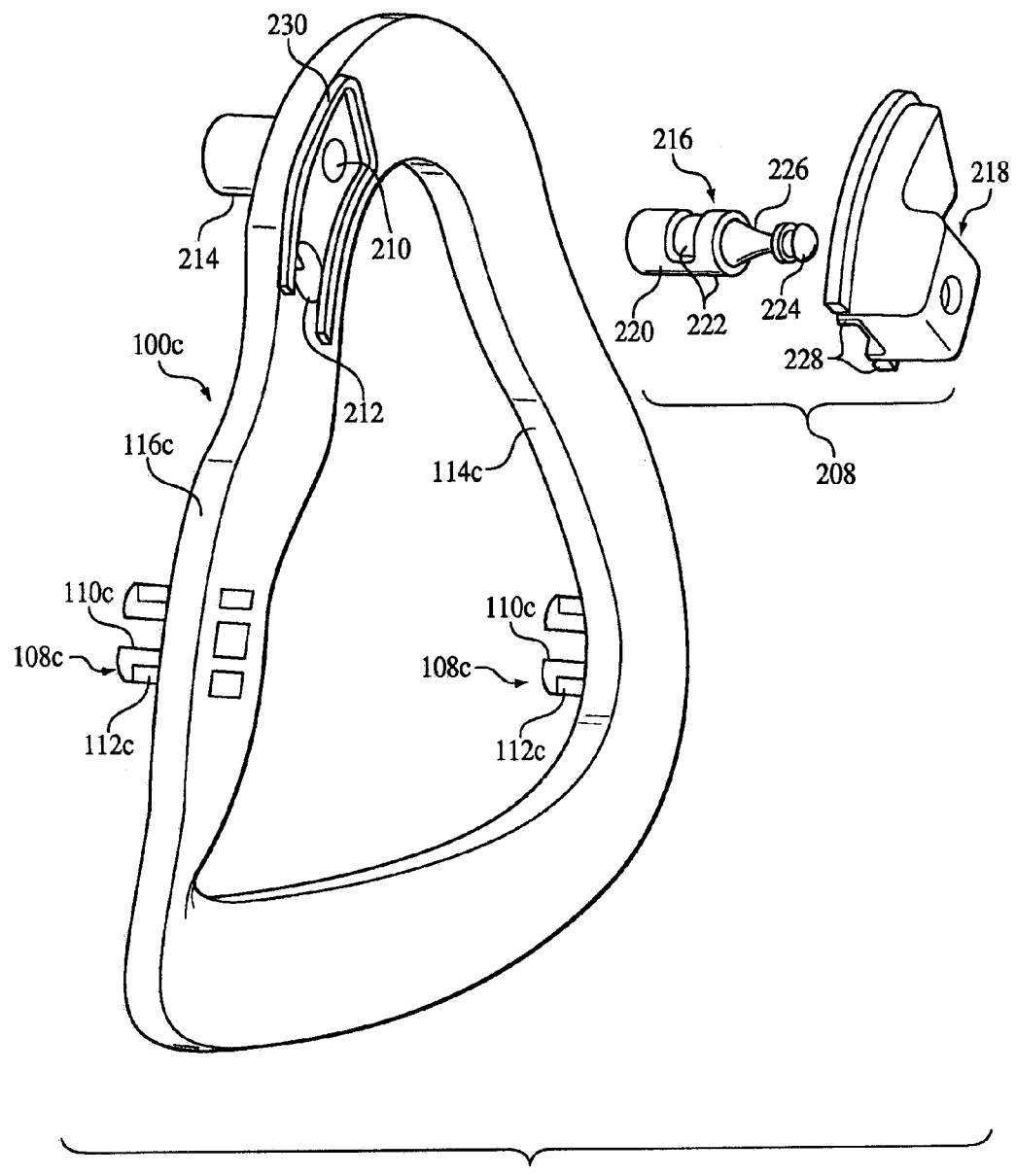
FIG. 24 is an exploded perspective of a retaining member and inflation/deflation valve of the respiratory mask of FIG. 21.
Figure 25:
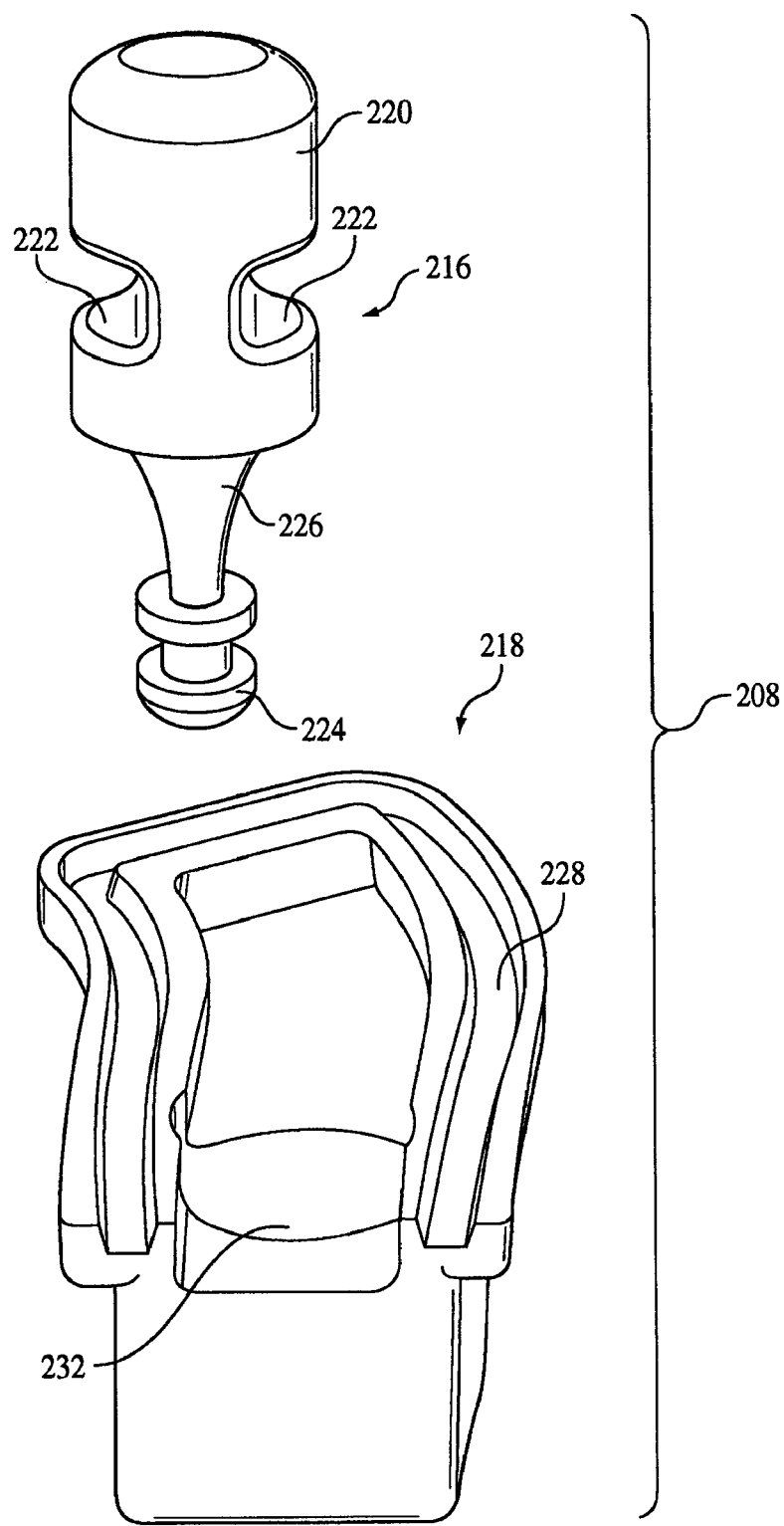
FIG. 25 is an exploded perspective view of the inflation/deflation valve shown in FIG. 24.

FIGS. 19 and 20 show an alternative embodiment of the latch wherein like parts are given the same reference number annotated with the letter "a." In this embodiment, latch 160a may be used with any of the embodiments of respiratory mask 10, 10a, 10b described in this disclosure but will be described with reference to respiratory mask 10 hereinafter for convenience. Latch 160a is typically provided as a two-piece component, comprising a latch body 162a and a post member 164a engaged with latch body 162a. Latch body 162a is typically a unitary structure having opposite sides or sidewalls 166a, 168a which are connected by a plurality of connecting members 170a. Connecting members 170a typically comprise a first connecting member 172a and a spaced apart second connecting member 174a extending between opposite side 166a, 168a. A third connecting member 176a also connects opposite sides 166a, 168a, and comprises a distal portion 177a that defines a central opening 178a through which post member 164a extends. First and second connecting members 172a, 174a are spaced apart to define a strap-receiving opening 182a therebetween in the same manner described previously.

In the present embodiment of latch 160a, third connecting member 176a may be considered to form the opposite sides 166a, 168a of latch body 162a. As shown in FIGS. 19 and 20, the opposite sides 166a, 168a of third connecting member 176a are generally angled inward toward Central Axis A passing though post member 164a to allow inward force to be applied to the opposite sides 166a, 168a of third connecting member 176a toward Central Axis A. Third connecting member 176a is further typically deformable to allow opposite sides 166a, 168b of third connecting member 176a to deflect toward Central Axis A. Third connecting member 176a includes a distal portion 177a adapted to deform axially along Central Axis A in a similar manner to distal portion 177a of third connecting member 176a discussed previously. In the present embodiment of latch 160a, third connecting member 176a is provided with finger grips 180a formed on opposite sides 166a, 168a for grasping by a user of respiratory mask 10 to adjust the positioning of latch 160a relative to track 44. Finger grips 180a are positioned to allow the user to apply force to opposing sides 166a, 168a of third connecting member 176a and cause the opposing sides 166a, 168a to deflect inward toward one another. As an inward "squeezing" force is applied to angled opposing sides 166a, 168a, distal portion 177a of third connecting member 176a depresses or moves toward second connecting member 174a thereby exposing an additional length of post member 164a through central opening 178a in distal portion 177a.

Post member 164a has a first end 184a adapted to engage second connecting member 174a and a second end 186a. First and second ends 184a, 186a of post member 164a are connected by a connecting shaft 188a in the manner described previously. Second end 186a is formed with a tapered ball detent 190a in the present embodiment of latch 160a. Tapered ball detent 190a comprises depending engagement tabs 192a for engaging engagement slots 46 in tracks 44. Tapered ball detent 190a may be replaced by a spherical structure similar to ball detent 190 described previously. Engagement tabs 192a are provided on opposite lower sides of tapered ball detent 190a for registering with engagement slots 46 in a releasable manner as described previously. First end 184a of post member 164a is secured in receiving opening 196a defined in second connecting member 174a by resiliently deflectable tabs 198a formed on first end 184a in generally the same manner as described previously, and thereby also permitting latch body 162a to pivot with respect to post member 164a.

Latch 160a is associated with track 44 by the user of respiratory mask 10 applying inward "squeezing" pressure on finger grips 180a. This inward pressure causes the angled opposite sides 166a, 168a of third connecting member 176a to move toward one another and simultaneously depresses distal portion 177a toward second connecting member 174a. An additional length of post member 164a will then be exposed from central opening 178a in distal portion 177a of third connecting member 176a. This depressing movement increases the length of post member shaft 188a exposed from central opening 178a. Tapered ball detent 190a on post member 164a may then be inserted into ball shaped (or correspondingly-shaped) opening 194 defined at one end of track 44. Typically, tapered ball detent 190a is oriented with engagement tabs 192a generally in line with adjustment slot 45 to allow tapered ball detent 190a and engagement tabs 192a to pass through opening 194. Once inserted into adjustment slot 45, additional clearance may again be provided by applying further "squeezing" pressure on opposite sides 166a, 168a of third connecting member 16a. This allows latch body 162a and post member 164a to be rotated to a position where engagements tabs 192a on tapered ball detent 190a may register with two opposed engagement slots 46 disposed on opposite sides of adjustment slot 45. The user may then release pressure on finger grips 180a which allows third connecting member 176a to resiliently return substantially to its initial orientation. When this occurs, distal portion 177a on third connecting member 176a will contact the outside surface of track 44 and post member 164a will withdraw axially in central opening 178a in distal portion 177a of third connecting member 176a. This retracting movement causes engagement tabs 192a on tapered ball detent 190a to engage engagement slots 46 in track 44, thereby securing latch body 162a in a specific position in track 44.

Distal portion 177a on third connecting member 176a will remain in contact with and apply a force against the outside surface of track 44 and prevent engagement tabs 192a from disengaging from engagement slots 46 until the user again applies "squeezing" force to finger grips 180a. When it is desired to move latch body 162a to a different position in track 44, the user again applies inward, "squeezing" pressure on finger grips 180a which again causes post member 164a to be exposed further from central opening 178a in distal portion 177a of third connecting member 176a. This movement lifts tapered ball detent 190a from contact with contact elements 47, and engagement tabs 192a to disengage from engagement slots 46. Latch body 162a and post member 164a may then be moved to a different position in adjustment slot 45. Once "squeezing" pressure is released with post member 164a disposed at the desired location in track 44, engagement tabs 192a will engage a new pair of opposed engagement slots 46 and tapered ball detent 190a will engage contact elements 47 in the vicinity of new engagements slots 46. Distal portion 177a of third connecting member 176a will again contact the outside surface of track 44 and apply a force against track 44 to prevent the disengagement of engagement tabs 192a from engagement slots 46. Although latches 160, 160a have been described in connection with the specific respiratory masks described herein, one of ordinary skill in the art can appreciate that latches 160, 160a could be used with a multitude of other masks without departing from the spirit or scope of the present invention.

Referring to FIGS. 21-29, another embodiment is shown wherein like parts have been given the same reference numbers annotated with the letter "c." The respiratory mask 10c differs from earlier embodiments set forth in this disclosure in that respiratory mask 10c is adapted to cover a wearer's nasal airway passages only. Accordingly, respiratory mask 10c is sized and shaped to encompass the human nose. Respiratory mask 10c includes the same general components as respiratory mask 10 described in detail hereinabove. Respiratory mask 10c therefore generally comprises a generally rigid support or base structure 12c and an inflatable rim or cushion 50c associated with base structure 12c. Inflatable rim 50c is attached to base structure 12c by a retaining member 100c that establishes a generally fluid tight seal between inflatable rim 50c and base structure 12c.

Base structure 12c is generally similar to base structure 12 described previously, comprising a base plate 14c having an outward facing or external side 16c and an internal side 18c to which inflatable rim 50c is secured. Internal side 18c is typically formed with inner and outer circumferentially or perimetrically-extending lips or rims 20c, 22c which project outward from internal side 18c and as act as inner and outer walls to restrain the inner and outer base areas of inflatable rim 50c. Base structure 12c defines the general nasal covering shape of respiratory mask 10c and is adapted to interface with external devices such as a hose or conduit for associating respiratory mask 10c with airflows containing anaesthetic, an oxygen supply, or with a CPAP device as examples.

Base plate 14c is formed with a bulbous nose covering portion 24c that projects outward on external side 16c of base plate 14c, and is generally sized and configured to accept and cover the wearer's nose such that the wearer's nasal airway passages are enclosed by respiratory mask 10c. Base plate 14c is formed with attachment flange 26c disposed radially about covering portion 24c. Inflatable rim 50c is secured to attachment flange 26c on the internal side 18c of base plate 14c in generally the same manner that inflatable rim 50 is attached to attachment flange 26 described previously. In particular, a "ringed" retaining member 100c is used to secured inflatable rim 50c to attachment flange 26c so that a generally fluid tight seal is established between inflatable rim 50c and attachment flange 26c. Covering portion 24c and attachment flange 26c are typically formed integrally as part of a unitary base plate 14c, but may also be separate elements as described previously. Base plate 14c may be formed from the same materials described previously in this disclosure.

Base plate 14c also typically includes a forehead extension 28c extending from a top end of attachment flange 26c. However, forehead extension 28c is now used as an attachment structure for attaching one or more securing straps to respiratory mask 10c used to secure respiratory mask 10c to the face of a wearer. Forehead extension 28c is typically formed integrally as part of base plate 14c in the manner described previously in this disclosure, but may be provided as a separate structure that is attached to base plate 14c. Forehead extension 28c defines two longitudinal slots 200 for attaching one or more attachment or securing straps to respiratory mask 10c, used to secure respiratory mask 10c to a wearer's face generally in the manner described previously in this disclosure. Forehead extension 29c may support a forehead cushion structure similar to forehead cushion 80 described previously.

Covering portion 24c is typically formed with a large central opening 30c. Central opening 30c is again provided as the main interface location or adaptation point for associating respiratory mask 10c with other devices. Accordingly, central opening 30c may be adapted to connect to a supply conduit for supplying oxygen and/or airflows containing anesthetic to respiratory mask 10, or to a positive air pressure supply conduit associated with a CPAP device. Additionally, central opening 30c may be adapted to accept a conduit or fixture used to connect to a supply conduit. An example of such a fixture is a 90° elbow 202 as illustrated. Covering portion 24c generally defines a concave internal cavity or recess 32c in internal side 18c of base plate 14c that is shaped to encompass the nose of the human face. Accordingly, with inflatable rim 50c secured to attachment flange 26c of base plate 14c, inflatable rim 50c is generally adapted to encompass the entire periphery of a wearer's nose. Attachment flange 26c also defines one or more tab receiving openings 40c for receiving attachment tabs 108c extending from the bottom side of retaining member 100c. The engagement of attachment tabs 108c with tab opening 40c is generally the same as that described previously in this disclosure.

Respiratory mask 10c is illustrated with a modified structure for inflating and deflating inflatable rim 50c. In respiratory mask 10c, attachment flange 26c defines an inlet/outlet opening 204 and valve opening 206. Valve opening 206 is adapted to receive an inlet/outlet valve 208, used to admit a fluidizing medium into inflatable rim 50c. As indicated, since inflatable rim 50c typically only comprises a single internal chamber 146c, the two openings provided in attachment flange 26c, namely inlet/outlet opening 204 and valve opening 206 are sufficient for admitting and removing the fluidizing medium from inflatable rim 50. Additional details of inlet/outlet valve 208 are provided hereinafter in this disclosure. The structure of respiratory mask 10 described previously having multiple internal chambers 146 may also be applied to respiratory mask 10c.

As with respiratory mask 10a described previously, respiratory mask 10c typically includes a single, continuous internal chamber or pocket 74c that is filled with a fluidizing medium to inflate or fill inflatable rim 50c. As with respiratory mask 10a, respiratory mask 10c comprises a bladder 52c with a main body portion 54c that is typically formed without internal dividers 72. As a result, bladder 52c and, more particularly, main body portion 54c of bladder 52c defines a single, continuous, and circumferentially-extending internal pocket 74c. Accordingly, bladder 52c is generally formed to have the same configuration as bladder 52a described previously, but is suitably sized and shaped as a nose-covering cushion. Additionally, it will be clear from viewing the various cross-sectional views in FIGS. 21-29 that base portion 60c of main body portion 54c has a thicker wall thickness than cushion portion 62c, but a less pronounced tapering area is provided between these portions in respiratory mask 10c.

Bladder 52c is generally adapted to engage with attachment flange 26c of base plate 14 via "ringed" retaining member 100c. Since a single internal pocket 74c is typically present in main body portion 54c of bladder 52c, retaining member 100c is not typically segmented but provided as a unitary ring structure or member. Additionally, retaining member 100c is also now formed with two openings, namely an inlet/outlet opening 210 and a valve opening 212, to coincide with inlet/outlet opening 204 and valve opening 206 in attachment flange 26c of base plate 14. Inlet/outlet opening 210 comprises an extended cylindrical section 214 that extends through inlet/outlet opening 204 in attachment flange 26c when retaining member 100c is assembled to base plate 14.

The assembly of respiratory mask 10c generally follows the assembly process described previously for respiratory mask 10, with some variations relating to inlet/outlet valve 208. Initially, inlet/outlet valve 208 is associated with retaining member 100c before retaining member 100c is joined to bladder 52c. Inlet/outlet valve 208 is typically a two-piece valve structure comprising a plug member 216 and a housing portion 218. Plug member 216 comprises a body portion 220 that defines two transverse slots 222 typically on opposing sides thereof. Plug member 216 further comprises a distal end tab 224 connected to body portion 220 by a resiliently deformable cone-shaped portion 226. Typically, plug member 216 is a unitary structure, having body portion 220, distal end tab 224, and cone-shaped portion 226 formed together as a unitary structure of molded plastic material. Typically, plug member 216 is formed of an elastic material such as silicone or thermal plastic elastomer to provide plug member 216 and, more particularly, cone-shaped portion 226 with resiliency analogous to a mechanical spring. Accordingly, plug member 216 could also be molded of hard plastic material having a metal spring associated therewith in place of cone-shaped portion 226.

Cone-shaped portion 226 is typically thin-walled to allow the cone-shaped portion 226 deform axially as axial force is applied to body portion 220. Housing portion 218 is adapted to be secured on the "internal" side of retaining member 100c that is received or inserted into bladder 52c. Housing portion 218 is a thin-walled housing structure defining an engagement groove 228 that is adapted to cooperate with a raised U-shaped lip or rim 230 extending from the "internal" side or retaining member 100c that cooperates with bladder 52c when assembled. The engagement of raised lip 230 with engagement groove 228 may be a friction fit/snap-fit connection or a suitable medical grade adhesive may used to secure this connection. Housing portion 218 further defines an opening 232 which is adapted to receive the distal end tab 224 on plug portion 216. Distal end tab 224 may engage opening 232 in housing portion 218 in a friction-fit/snap-fit manner.

To assemble inlet/outlet valve 208 to retaining member 100c, housing portion 218 is joined via engagement groove 228 to raised lip 230 on retaining member 100c. Plug member 216 is then inserted into valve opening 212 in retaining member 100c and distal end tab 224 is inserted into corresponding engagement opening 232 in housing 218. Inlet/outlet valve 208 is now supported on retaining member 100c and retaining member 100c may join to bladder 52c. Retaining member 100c is joined to bladder 52c by inserting retaining member 100c into the general U-shaped transverse cross-section defined by bladder 52c, with housing portion 218 of inlet/outlet valve 208 received in internal pocket 74c of bladder 52c. Attachment tabs 108c projecting from retaining member 100c will face outward from bladder 52c. As retaining member 100c is inserted into bladder 52c, opposing flanges 64c wrap around retaining member 100c and upstanding lips 66c on flanges 64c engage grooves 118c defined by inner and outer peripheral lips 114c, 116c on retaining member 100c. Additionally, inner and outer peripheral lips 114c, 116c on retaining member 100c correspondingly engage grooves 68c defined by upstanding lips 66c on flanges 64c, thereby forming overlapping engagements between retaining member 100c and main body portion 54c of bladder 52c, as described previously in this disclosure. With bladder 52c now joined with retaining member 100c, this component structure may be joined to attachment flange 26c of base plate 14c in generally the manner described previously in this disclosure to finish assembly of respiratory mask 10c.

Figure 29A:
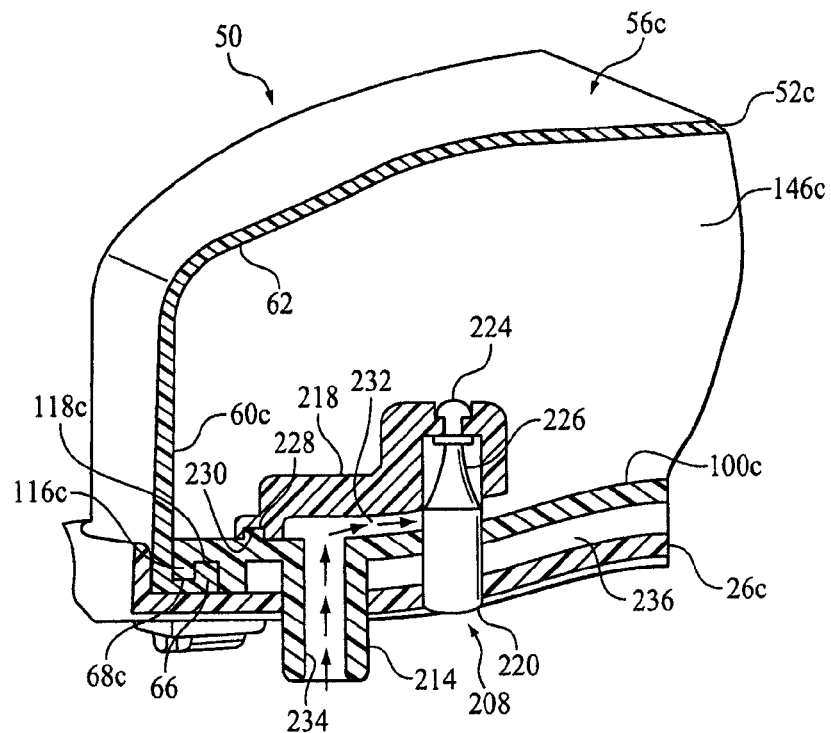
FIG. 29A is a cross-sectional view of a portion of the respiratory mask of FIG. 21 showing the inflation/deflation valve of the mask in a closed position.
Figure 29B:
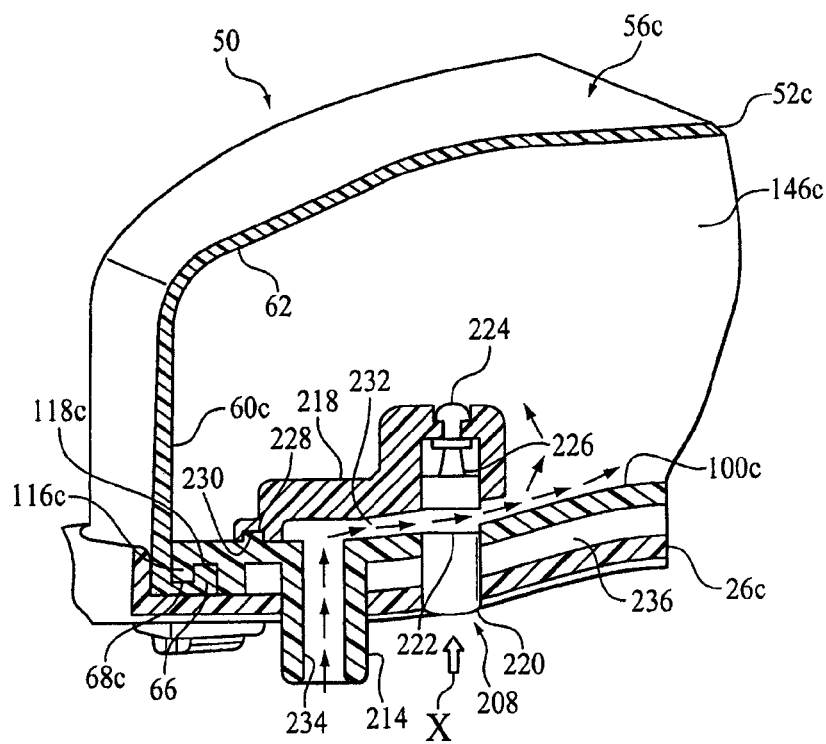
FIG. 29B is a cross-sectional view of the portion of the respiratory mask shown in FIG. 29A showing the inflation/deflation valve in an open position.

As shown in FIGS. 29A and 29B, inflation/deflation valve 208 operates to selectively block an inlet/outlet passage 234 defined by cylindrical section 214 extending from inlet/opening 210 of retaining member 100c and housing portion 218. In a closed position, as shown in FIG. 29A, body portion 220, which is not shown in cross-section in FIGS. 29A and 29B, blocks flow of fluidizing medium (represented by arrows) into internal chamber 146c defined by bladder 52c and base plate 14c. In the closed position, transverse slots 222 are located in an intermediate cavity 236 defined between attachment flange 26c and retaining member 100c, allowing body portion 220 to block inflow of fluidizing medium. FIG. 29B shows inflation/deflation valve 208 in an open state allowing inflow and outflow of fluidizing medium from internal chamber 146c. Inflation/deflation valve 208 is opened by applying pressure in the direction of arrow X on body portion 220. The axial pressure will cause cone-shaped portion 226 to compress axially, thereby allowing transverse slots 222 in body portion 220 become aligned with inlet/outlet passage 234. Fluidizing medium may then enter internal chamber 146c and, further, exit internal chamber 146c via inlet/outlet passage 232. Due to the relatively large passage defined by inlet/outlet passage 234 and the relatively large transverse slots 222 in body portion 220, this inflation/deflation valve is suitable for admitting/removing liquid fluidizing mediums such as mineral oil, saline solution, highly viscous gel or a combination of liquid/gaseous fluidizing medium, in addition to completely gaseous fluidizing medium. A solid fluidizing medium, for example in powder form, may be employed as well. Once axial pressure is released on body portion 220, cone-shaped portion 226 resiliently returns substantially to its initial state and the transverse slots 222 in body portion 220 are again unaligned with inlet/outlet passage 232. As shown, cylindrical section 214 extending from inlet/outlet opening 212 on retaining member 100c extends sufficiently outward from the external side 16 of base plate 14 that a supply conduit, such as hose, for the fluidizing medium may be connected to cylindrical section 214. The configuration of inlet/outlet valve 208 may be applied to any of respiratory masks 10, 10a, 10b described in this disclosure in place of inflation valves 150.

Furthermore, when inflatable rim 50 according to any of the embodiments of respiratory masks 10, 10a, 10b described in this disclosure is filled with a gaseous fluidizing medium, a pressure relief valve (not shown) may be provided extending through attachment flange 26 and retaining member 100 for preventing over-inflation of internal chamber 146 and setting a top end to inflation pressure within each internal chamber 146 if desired. Each internal chamber 146 is typically provided with such a pressure relief valve, and could be provided in place of inflation valves 150 or as part of inflation valves 150.

Figure 13C:
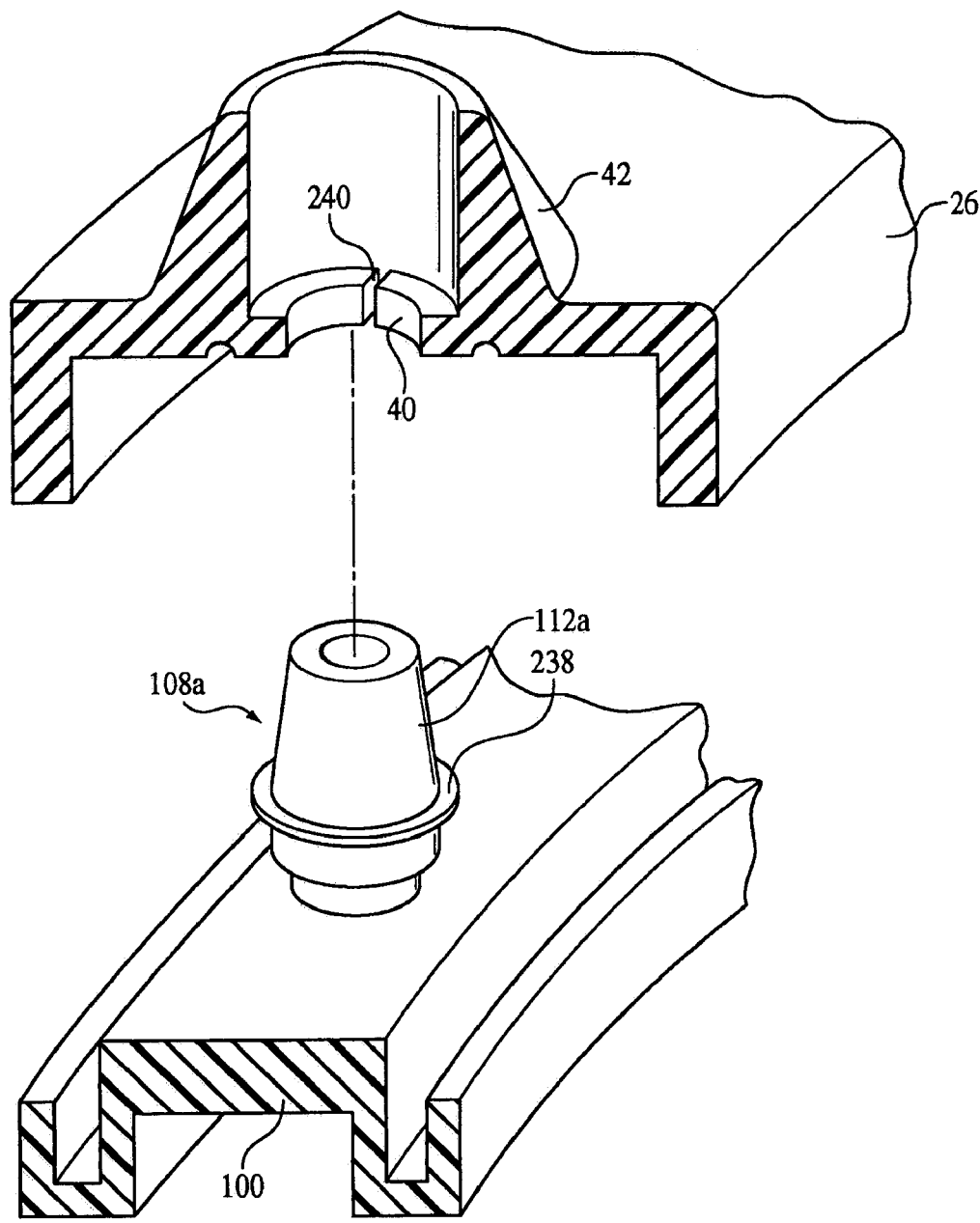
FIG. 13C is a perspective and partial cross-sectional view showing an alternative embodiment of the mechanical attachment mechanism.
Figure 13D:
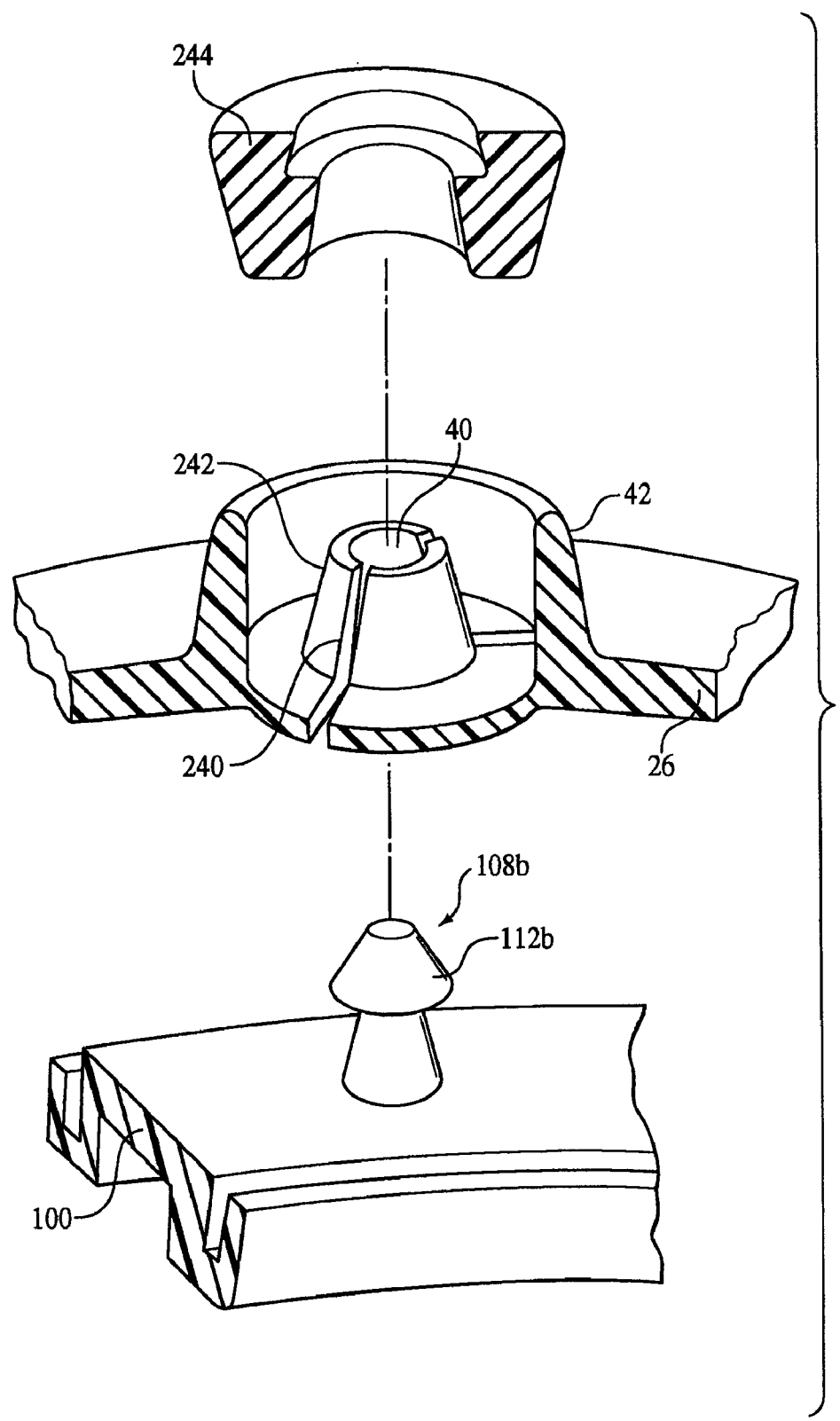
FIG. 13D is a perspective and partial cross-sectional view showing an embodiment of the mechanical attachment mechanism.

Finally, FIGS. 13C and 13D show additional alternative forms of attachment tabs 108 discussed previously in connection with FIGS. 13A and 13B. In FIG. 13C, attachment tab 108a comprises a unitary generally frustum-shaped prong head 112a adapted to engage tab opening 40 in attachment flange 26 of base plate 14. Prong head 112a further comprises a sealing flap 238 for sealing tab opening 40 when prong head 112a is inserted through opening 40. Attachment flange 26 may define one or more grooves or splits 240 extending from tab opening 40, as shown in FIG. 13C, to allow sufficient flexure of attachment flange 26 to allow prong head 112a to project through opening 40 when respiratory mask 10 is assembled. FIG. 13D shows a further variation of attachment tab 108b which again has a generally frustum-shaped prong head 112b adapted to engage tab opening 40 in attachment flange 26. Attachment flange 26, as shown in FIG. 13D, may comprise and additional raised tab rim 242 within raised tab rim 42 (shown in FIGS. 13A and 13B) for engagement by prong head 112b. Again, attachment flange 26 may define one or more grooves or splits 240 extending from tab opening 40, as shown in FIG. 13D, to allow sufficient flexure of attachment flange 26 to allow prong head 112b to project through tab opening 40 when respiratory mask 10 is assembled. A sealing plug 244 may be inserted into raised tab rim 42 to further seal tab opening 40. Sealing plug 244 may snap fit onto prong head 112b and tab rim 242, if desired.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims. Moreover, the features of one embodiment may be combined with the features of any of the other embodiments without departing from the scope of the present invention.

What is claimed is:

1. A respiratory mask, comprising:
a base plate adapted for connection to a gas source, the base plate having an inflation opening formed therein; and
an inflatable bladder secured to the base plate to form a generally fluid tight seal with the base plate and defining at least one internal chamber with the base plate, wherein a fluidizing medium may be admitted into the at least one internal chamber through the inflation opening to fill the bladder and form a resilient cushion, and wherein the fluidizing medium may be withdrawn from the at least one internal chamber through the inflation opening, wherein the bladder is secured to the base plate by a retaining member, the bladder comprising at least one internal divider to define a plurality of internal chambers with the base plate, and wherein the retaining member is segmented to correspond to the number of internal chambers defined by the base plate and bladder.

2. A respiratory mask as claimed in claim 1, the bladder comprising a unitary body defining a generally U-shaped transverse cross-section comprising a base portion and a cushion portion, and the base portion comprising a wall thickness greater than the cushion portion.

3. A respiratory mask as claimed in claim 1, wherein the bladder comprises a sealing flap for sealing against a mask-wearer's skin.

4. A respiratory mask as claimed in claim 1, wherein the retaining member is mechanically engaged with the base plate or bonded to the base plate.

5. A respiratory mask as claimed in claim 1, further comprising a valve associated with the inflation opening for filling the at least one internal chamber with the fluidizing medium.

6. A respiratory mask as claimed in claim 1, wherein the bladder comprises a non-uniform wall thickness.

7. A respiratory mask as claimed in claim 1, the bladder comprising a unitary body defining a generally U-shaped transverse cross-section comprising a base portion and a cushion portion, and wherein at least a portion of the base portion is secured to the base plate to form the generally fluid tight seal with the base plate.

8. A respiratory mask as claimed in claim 1, wherein the at least one internal divider is adapted to permit fluid communication between the internal chambers.

9. A respiratory mask, comprising:
a base plate adapted for connection to a gas source, the base plate having an inflation opening formed therein;
a retaining member; and
an inflatable bladder secured to the base plate by the retaining member, the retaining member securing the bladder to the base plate such that the bladder forms a generally fluid tight seal with the base plate and defines at least one internal chamber with the base plate, wherein a fluidizing medium may be admitted into the at least one internal chamber through the inflation opening to fill the bladder and form a resilient cushion, and wherein the fluidizing medium may be withdrawn from the at least one internal chamber through the inflation opening, the bladder comprising a unitary body defining a generally U-shaped transverse cross-section comprising a base portion and a cushion portion, and wherein at least a portion of the base portion is sandwiched between the retaining member and base plate to form the generally fluid tight seal with the base plate.

10. A respiratory mask as claimed in claim 9, wherein the bladder comprises a non-uniform wall thickness.

11. A respiratory mask as claimed in claim 9, the bladder comprising at least one internal divider to define a plurality of internal chambers with the base plate.

12. A respiratory mask as claimed in claim 9, the base portion comprising a wall thickness greater than the cushion portion.

13. A respiratory mask as claimed in claim 9, wherein the retaining member is mechanically engaged with the base plate or bonded to the base plate.

14. A respiratory mask, comprising:
a base plate adapted for connection to a gas source, the base plate having an inflation opening formed therein; and
an inflatable bladder secured to the base plate to form a generally fluid tight seal with the base plate and defining at least one internal chamber with the base plate, wherein a fluidizing medium may be admitted into the at least one internal chamber through the inflation opening to fill the bladder and form a resilient cushion, and wherein the fluidizing medium may be withdrawn from the at least one internal chamber through the inflation opening, the base plate comprising a forehead extension, and wherein the bladder is formed to encompass the forehead extension.

15. A respiratory mask as claimed in claim 14, wherein the bladder is secured to the forehead extension by a forehead retaining member.

16. A respiratory mask, comprising:
a base plate adapted for connection to a gas source, the base plate having an inflation opening formed therein;
a retaining member; and
an inflatable bladder secured to the base plate by the retaining member, the retaining member securing the bladder to the base plate such that the bladder forms a generally fluid tight seal with the base plate and defines at least one internal chamber with the base plate, wherein a fluidizing medium may be admitted into the at least one internal chamber through the inflation opening to fill the bladder and form a resilient cushion, and wherein the fluidizing medium may be withdrawn from the at least one internal chamber through the inflation opening, wherein the base plate further includes at least one track, and wherein the respiratory mask further includes at least one latching mechanism adapted to engage the track, the latching mechanism including a latch body and a post member wherein the latch body biases the post member into engagement with at least one engagement slot.

* * * * *